United States Patent
Shah

(10) Patent No.: US 10,490,304 B2
(45) Date of Patent: Nov. 26, 2019

(54) DEVICE-DRIVEN NON-INTERMEDIATED BLOCKCHAIN SYSTEM OVER A SOCIAL INTEGRITY NETWORK

(71) Applicant: Netspective Communications LLC, Silver Spring, MD (US)

(72) Inventor: Shahid N. Shah, Silver Spring, MD (US)

(73) Assignee: Netspective Communications LLC, Silver Spring, MD (US)

( * ) Notice: Subject to any disclaimer, the term of this patent is extended or adjusted under 35 U.S.C. 154(b) by 512 days.

(21) Appl. No.: 15/372,699

(22) Filed: Dec. 8, 2016

(65) Prior Publication Data
US 2017/0091397 A1    Mar. 30, 2017

Related U.S. Application Data

(63) Continuation-in-part of application No. 13/740,381, filed on Jan. 14, 2013, now abandoned.
(Continued)

(51) Int. Cl.
*G16H 10/60* (2018.01)
*H04L 29/06* (2006.01)
(Continued)

(52) U.S. Cl.
CPC ............ *G16H 10/60* (2018.01); *G06Q 50/01* (2013.01); *G06Q 50/22* (2013.01); *H04L 9/3236* (2013.01);
(Continued)

(58) Field of Classification Search
None
See application file for complete search history.

(56) References Cited

U.S. PATENT DOCUMENTS 7,426,475 B1    9/2008  Tangellapally et al.
7,440,904 B2   10/2008  Hasan et al.
(Continued)

OTHER PUBLICATIONS

Broderson et al., Blockchain: Securing a New Health Interoperability Experience, Aug. 2016, accenture LLP, https://newsroom.accenture.com/industries/health-public-service/accenture-finds-information-governance-framework-needed-to-guide-e-health-investments-and-strategy.htm (Year: 2016).*

*Primary Examiner* — Devin C Hein
(74) *Attorney, Agent, or Firm* — Rahman LLC

(57) ABSTRACT

A blockchain configured device-driven disintermediated distributed system for facilitating multi-faceted communication over a network. The system includes entities connected with a communications network. Each of the entities and associated devices and sensors and networks serve as a source of data records. The system includes a blockchain configured data bank accessible by each of the plurality of entities based on rules and preferences of the entities upon authorization by the blockchain configured data bank. The blockchain configured data bank includes a processing component for executing stored instructions to process the data records of the entities over the communications network. The system includes a blockchain configured component communicatively coupled to the blockchain configured data bank and adapted to be accessible by each of the plurality of entities. The system includes a validation device including a facial expression-based validation device and a geo-tagging-based validation device.

14 Claims, 11 Drawing Sheets

Related U.S. Application Data

(60) Provisional application No. 61/590,914, filed on Jan. 26, 2012.

(51) Int. Cl.
*G06Q 50/00* (2012.01)
*G06Q 50/22* (2018.01)
*H04L 9/32* (2006.01)

(52) U.S. Cl.
CPC .......... *H04L 63/102* (2013.01); *H04L 63/107* (2013.01); *H04L 63/20* (2013.01); *H04L 2209/38* (2013.01); *H04L 2209/56* (2013.01)

(56) References Cited

U.S. PATENT DOCUMENTS

| | | |
|---|---|---|
| 7,603,413 B1 | 10/2009 | Herold et al. |
| 7,739,123 B1 | 6/2010 | Rappaport |
| 8,244,848 B1 | 8/2012 | Narayanan et al. |
| 2002/0010679 A1 | 1/2002 | Felsher |
| 2004/0034550 A1 | 2/2004 | Menschik et al. |
| 2004/0186746 A1 | 9/2004 | Angst et al. |
| 2005/0187794 A1 | 8/2005 | Kimak |
| 2006/0004588 A1 | 1/2006 | Ananda |
| 2006/0095296 A1 | 5/2006 | Erdman |
| 2006/0229918 A1 | 10/2006 | Fotsch |
| 2007/0078686 A1 | 4/2007 | Dettinger et al. |
| 2007/0162295 A1 | 7/2007 | Akhtar et al. |
| 2007/0282912 A1 | 12/2007 | Reiner |
| 2008/0040673 A1 | 2/2008 | Zuckerberg et al. |
| 2008/0046292 A1 | 2/2008 | Myers et al. |
| 2008/0270438 A1 | 10/2008 | Aronson et al. |
| 2008/0271109 A1* | 10/2008 | Singh ................... H04L 63/08 726/1 |
| 2009/0276463 A1 | 11/2009 | Miller |
| 2009/0292814 A1 | 11/2009 | Ting et al. |
| 2010/0203909 A1 | 8/2010 | Oldach |
| 2010/0306183 A1 | 12/2010 | Laconi |
| 2011/0218824 A1 | 9/2011 | Pavlatos et al. |
| 2012/0072234 A1 | 3/2012 | Rao |
| 2012/0245958 A1 | 9/2012 | Lawrence et al. |
| 2013/0115915 A1* | 5/2013 | Tipton ................. H04W 12/08 455/411 |
| 2017/0011195 A1* | 1/2017 | Arshad ............... G06F 19/3456 |
| 2017/0039330 A1* | 2/2017 | Tanner, Jr. ............. G06F 19/00 |
| 2018/0082023 A1* | 3/2018 | Curbera ............... H04L 9/3236 |
| 2018/0082024 A1* | 3/2018 | Curbera ............... H04L 9/3236 |

* cited by examiner

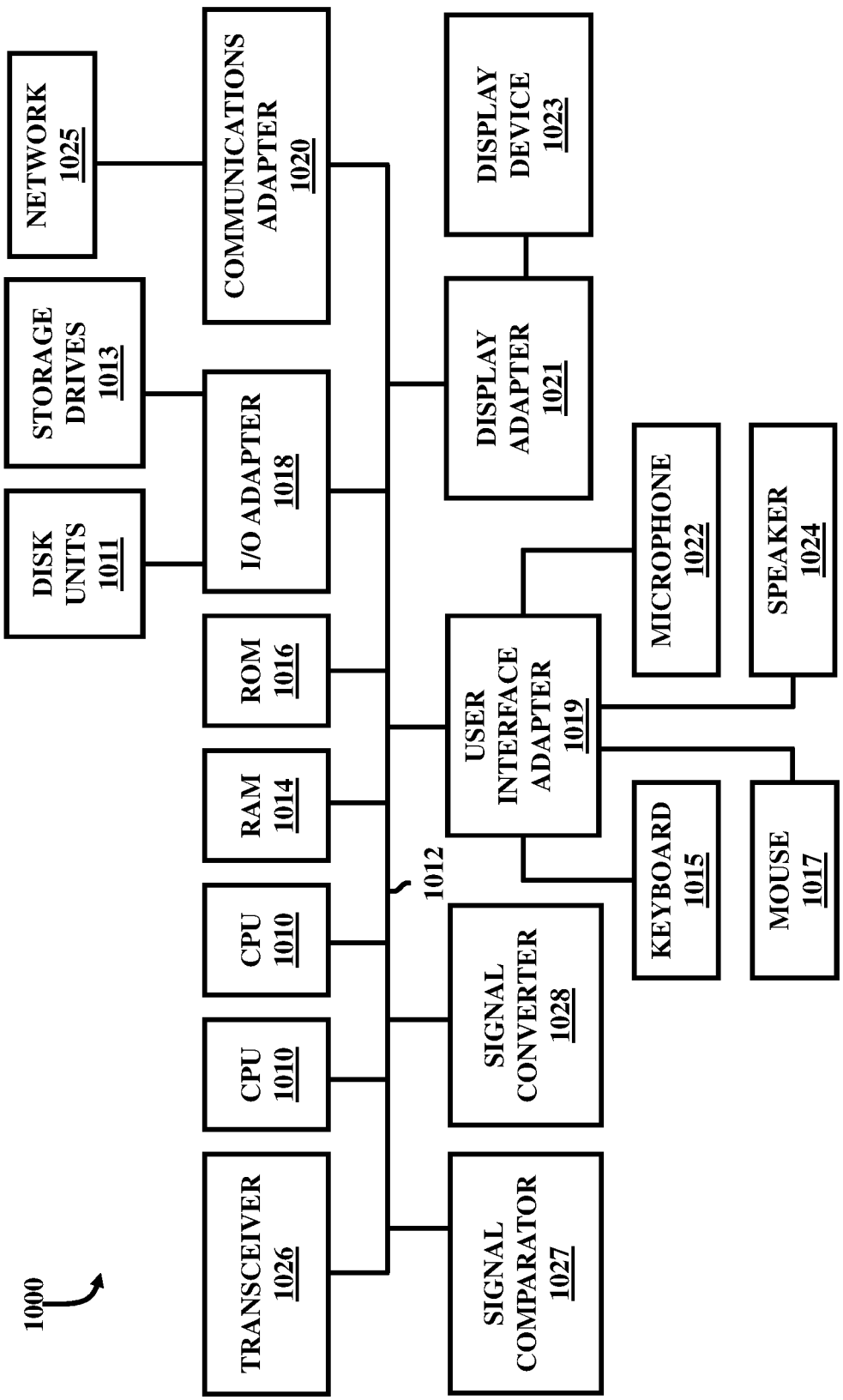

DEVICE-DRIVEN NON-INTERMEDIATED BLOCKCHAIN SYSTEM OVER A SOCIAL INTEGRITY NETWORK

CROSS-REFERENCE TO RELATED APPLICATIONS

This application is a continuation-in-part of U.S. patent application Ser. No. 13/740,381 filed on Jan. 14, 2013, which claims priority to U.S. Provisional Application No. 61/590,914, filed on Jan. 26, 2012, the complete disclosures of which, in their entireties, are herein incorporated by reference.

BACKGROUND

Technical Field

The embodiments herein generally relate to blockchain configured systems and more particularly to blockchain configured management systems.

Description of the Related Art

Hospitals, caretakers, nursing centers or homes, medical offices, medical centers, or other sources of medical care and entities generally keep medical and demographic or other such records of their patients. These records may include a variety of information such as demographic information of their patients, medical history, diagnostic and pathology reports of their patients, medical reports or prescriptions, device generated information, or other such information. This information can be used for a variety of purposes by these sources of medical care. A few examples of them are, without limitations, tracking of the patients and their records, billing, historical assessments, integrating with medical devices, remote care, future care taking, telemedicine, proper ongoing medical or health assessment or treatment, or any other similar purpose.

One way to collate and store the medical data is with the use of an electronic health record data bank (EHRDB). These records from various entities can be electronically maintained such as by the electronic health record data bank (EHRDB) in a central system accessible by the entities. The EHRDB may store medical data of the entities and retrieve the data of the respective entities as and when requested by them.

There is a need for an improved system and a method that provides a multi-faceted facility in the EHRDB to interact with several entities simultaneously over a blockchain configured framework for advanced security and smooth interaction without requiring human intermediation.

SUMMARY

In view of the foregoing, an embodiment herein provides a blockchain validation system. The blockchain validation system includes a plurality of computing systems connected with a social integrity network and a plurality of sub-systems of data records. The plurality of sub-systems include a plurality of social aware networks, a plurality of sensors, a plurality of wearable devices, and a plurality of scanners. Each of the plurality of social aware networks, plurality of sensors, plurality of wearable devices, and plurality of scanners serve as a provider of the data records. The blockchain validation system further includes a blockchain configured data bank (BCDB) hosted on a server accessible by each of the plurality of computing systems based on rules and preferences of a plurality of entities upon authorization by the BCDB. The plurality of entities subscribe with the BCDB to create, store, edit, manage or control the data records. The BCDB includes a computer processing component executing stored computer-implemented instructions to process the data records of the plurality of entities over the social integrity network. The data records are obtained from the plurality of social aware networks, plurality of sensors, plurality of wearable devices, and the plurality of scanners associated with the entities. The BCDB further includes a hardware repository coupled to the BCDB to store the data records of the plurality of entities collected from the plurality of social aware networks, plurality of sensors, plurality of wearable devices, and the plurality of scanners. The blockchain validation system includes a blockchain configured component communicatively coupled to the BCDB and adapted to be accessible by each of the plurality of computing systems such that the blockchain configured component enables social interaction among the entities by bypassing the BCDB, and communication with the BCDB over the social integrity network for data records transfer. The blockchain validation system includes a plurality of blockchain configured social federation proxies communicatively coupled to the BCDB and the social integrity network and configured to retrieve the data records from the BCDB collected from the plurality of social aware networks, plurality of sensors, plurality of wearable devices, and the plurality of scanners, and distribute them to the plurality of social aware networks and the plurality of computing systems for display to the respective plurality of entities upon request and validation. The plurality of blockchain configured social federation proxies may include a virtualization layer to provide a distributed virtual access of storage of the data records retrieved from the BCDB and allow an indirect access of the plurality of entities to the BCDB. The plurality of blockchain configured social federation proxies include a processing device configured to manage and communicate the data records in a blockchain configured distributed framework. The blockchain validation system includes a blockchain validation device configured to receive digital inputs from the BCDB to identify access rules and execute blockchain validation mechanisms to authorize the plurality of entities to access the data records accessible from the blockchain configured component through the distributed plurality of blockchain configured social federation proxies linked to the BCDB simultaneously. The blockchain validation device includes a face recognition device to process information received from respective facial expression sensors associated with the plurality of entities to verify identity of the plurality of entities based on respective facial expressions. The blockchain validation device includes a geo-tagging device to obtain geographical coordinates from respective global position system (GPS)-based devices associated with the plurality of entities, tag the data records using geo-tags to establish a geographical identity with the data records, and validate identity of the plurality of entities and the respective data records based on geographical patterns. The BCDB and the plurality of blockchain configured social federation proxies are further configured to identify a source and a target, wherein the source identifies data records for sharing and the target identifies a computing system out of the plurality of computing systems as a recipient of the data records defined by the source. The identification of at least one of the source and the target is dependent on (a) a permission from an owner of the source, (b) an indication of an extent of sharing, (c) a nature and characteristic of the target, (d) a purpose of the sharing of the data records to the target, (e) a timeframe for allowance of sharing of the data records. The source and the target are determined based on (a) to (e) upon receipt of a request from the owner entity. The sharing of the data records with the target is limited to the timeframe. The BCDB and the plurality of blockchain configured social federation proxies are further configured to allow partial viewing of the data records corresponding to the source by the target based on (a) to (e), stop any viewing based on (a) to (e), select which parts to view based on (a) to (e), determine or facilitate the owner entity of the data records to determine who has viewed the data records and accordingly redefine said (a) to (e) and also accordingly make a decision about the partial viewing of the data records corresponding to the source by the target based on (a) to (e) and stopping of any viewing or selecting which parts to view based on the redefined (a) to (e). The blockchain configured component is configured to identify who has viewed the data records in real time and share information about who has viewed the data records with the owner in real time, such that the owner allows fully or partially or stops viewing of the data records by the target in real time.

BRIEF DESCRIPTION OF THE FIGURES

In the drawings, like numerals describe similar components substantially throughout the several views. The drawings illustrate generally, by way of an example, but not by a way of limitation, various embodiments.

FIG. 10 illustrates a computer system that may be used in accordance with the embodiments herein.

DETAILED DESCRIPTION

Figure 1:
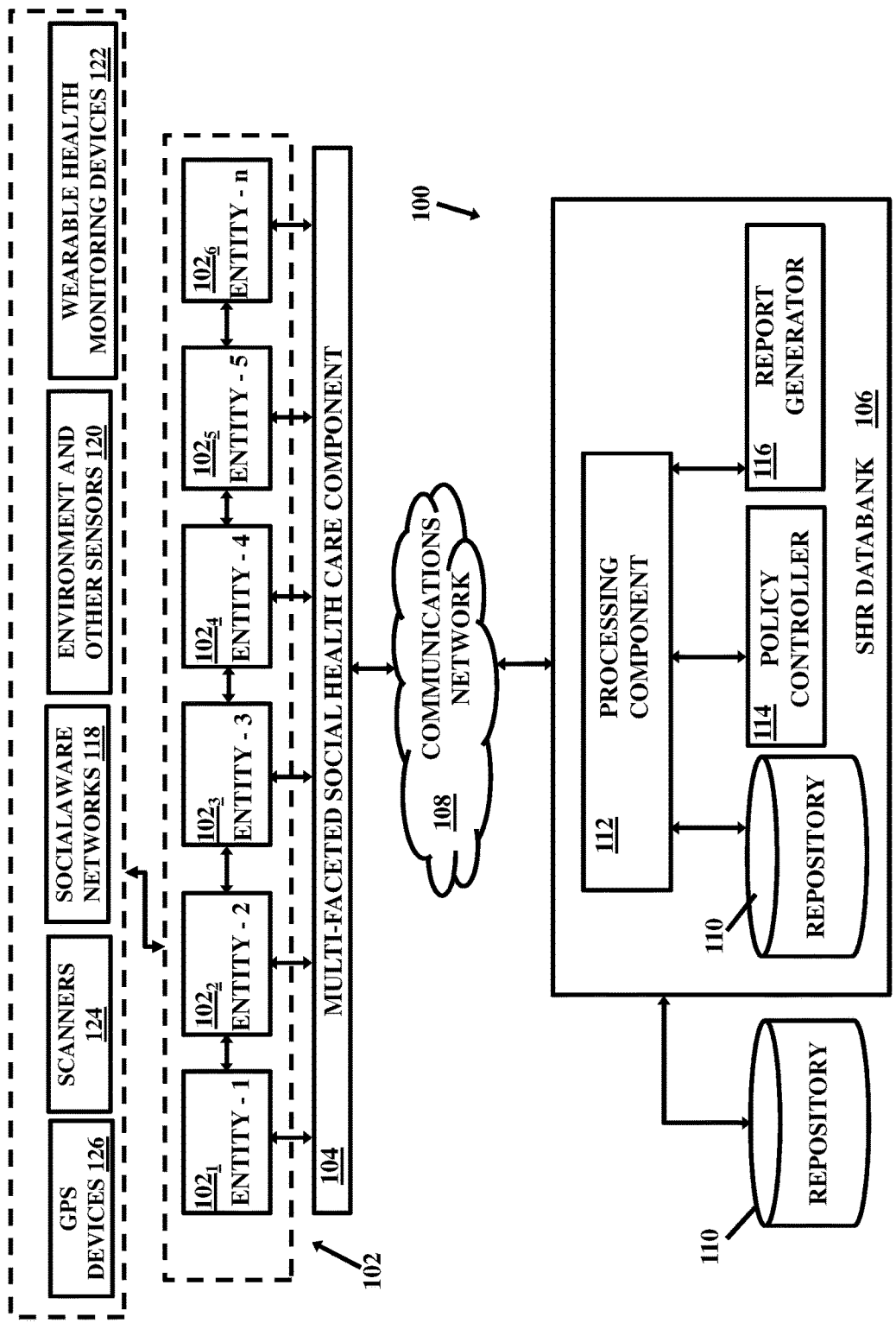
FIG. 1 illustrates generally, but not by the way of limitation, among other things, a schematic diagram depicting a communications environment, in which some embodiments herein may operate.

The embodiments herein and the various features and advantageous details thereof are explained more fully with reference to the non-limiting embodiments that are illustrated in the accompanying drawings and detailed in the following description. Descriptions of well-known components and are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

In the following detailed description, reference is made to the accompanying drawings that form a part hereof, and these are shown by way of illustrating specific embodiments herein that may be practiced. These embodiments, which are also referred to herein as "examples," are described in sufficient detail to enable those skilled in the art to practice the embodiments herein, and it is to be understood that the embodiments may be combined, or that other embodiments may be utilized and that structural, logical, and electrical changes may be made without departing from the scope of the embodiments herein.

In this document, the terms "a" or "an" are used, as is common in patent documents, to include one or more than one. In this document, the term "or" is used to refer to a "nonexclusive or" unless otherwise indicated.

In an exemplary embodiment, the various modules described herein and illustrated in the figures are embodied as hardware-enabled modules and may be configured as a plurality of overlapping or independent electronic circuits, devices, and discrete elements packaged onto a circuit board to provide data and signal processing functionality within a computer. An example might be a comparator, inverter, or flip-flop, which could include a plurality of transistors and other supporting devices and circuit elements. The modules that are configured with electronic circuits process computer logic instructions capable of providing digital and/or analog signals for performing various functions as described herein. The various functions can further be embodied and physically saved as any of data structures, data paths, data objects, data object models, object files, database components. For example, the data objects could be configured as a digital packet of structured data. The data structures could be configured as any of an array, tuple, map, union, variant, set, graph, tree node, and an object, which may be stored and retrieved by computer memory end may be managed by processors, compilers, and other computer hardware components. The data paths can be configured as part of a computer CPU that performs operations and calculations as instructed by the computer logic instructions. The data paths could include digital electronic circuits, multipliers, registers and buses capable of performing data processing operations and arithmetic operations (e.g., Add, Subtract, etc.), bitwise logical operations (AND, OR, XOR, etc.), bit shift operations (e.g., arithmetic, logical, rotate, etc.), complex operations (e.g., using single clock calculations, sequential calculations, iterative calculations, etc.). The data objects may be configured as physical locations in computer memory and can be a variable, a data structure, or a function. In the embodiments configured as relational databases (e.g., such Oracle® relational databases), the data objects can be configured as a table or column. Other configurations include specialized objects, distributed objects, object oriented programming objects, and semantic web objects, for example. The data object models can be configured as an application programming interface for creating HyperText Markup Language (HTML) and Extensible Markup Language (XML) electronic documents. The models can be further configured as any of a tree, graph, container, list, map, queue, set, stack, and variations thereof. The data object files are created by compilers and assemblers and contain generated binary code and data for a source file. The database components can include any of tables, indexes, views, stored procedures, and triggers.

The embodiments herein provide a method and system for creating, controlling and managing portions of health care records more specifically electronic health care records via a multi-faceted social health care component to enable social interaction among one or more entities (hereafter entities). The multi-faceted social health care component is configured to allow collaboration and interaction among the entities through a Social Health Record Data Bank (SHRDB). The SHRDB can be configured to provide a repository for the storage of a plurality of such as electronic healthcare records generated by the entities. The various portions of the multi-faceted social health care component can be accessed by the entities based on entity specific preferences and roles. In accordance with some embodiments, the entities may be communicatively connected among themselves. For example, the entities can interact through emailing, Instant Messaging, or various other modes. In some embodiments, the entities can connect or interact among themselves even without going through the SHRDB (thus bypassing the SHRDB).

In an embodiment, the medical records or health records can be social health records or social records simply. The social health records referred herein can be understood as medical records stored in a central or distributed storage database such as the SHRDB and associated proxy locations. In an embodiment, the social health records referred herein can be understood as medical records collected from several distinct locations such as several social aware networks or applications or devices or sensors or other information sources (also referred to as data sources interchangeably without limitations) and brought at a single location such as the SHRDB or ad distributed setup such as the SHRDB and associated proxy locations such as a social federation proxy. The social records thus collected and integrated at these locations can further be distributed socially among several entities such as users individually or through social networks or applications. Therefore, the present system and method provides a mechanism for two-way communication between several entities and/or devices and the social aware networks wherein the records can be collected from the social aware networks or applications or devices or input by the entities as well as distributed toward the social aware networks or applications or devices or to the entities. In such embodiments, the social records can be considered as the medical records floated over a network for allowance toward such a two-way communication.

In various embodiments discussed below, the terms 'medical records', 'health records', 'social records', 'electronic records', 'medical health records', 'social health records' are interchangeably used without limitations. The terms entities and users are used interchangeably without limitations. The terms social aware network, and social network are used interchangeably without limitations. The terms 'data' and 'record' are used interchangeably without limitations.

In some embodiments, the multi-faceted social health care component can be a blockchain configured multi-faceted social health care component, the SHRDB can be a blockchain configured SHRDB, the social federation proxy and/or other proxy locations can be blockchain configured social federation proxy locations, and entire system can be completely or partially blockchain configured distributed over a social integrity network as discussed later at least in conjunction with some embodiments.

The blockchain configured digital ecosystem and associated components provided by the embodiments herein, also referred to as a "smart contract based distributed integrity network" does not require a centralized health information exchange (HIE) operator because all participants may have access to distributed ledgers to maintain a secure exchange without broken trusts. This allows disintermediation by removing human participants from a chain of the participants such as entities. Additionally, the health data records are distributed across a plurality of storage locations in the blockchain accessible by the participants simultaneously and allowing the ability to make updates almost in real time. The blockchain configured digital ecosystem provides a secured, disintermediated and distributed framework to amplify and support integration of healthcare information across a range of uses and stakeholders defined by the entities. The blockchain configured digital ecosystem facilitates a secured and distributed framework for patient digital identities to allow access to body worn personally connected health devices, connected health devices at home and other facilities, storage devices and servers hosting the medical records and the like, with the use of private and public encryption/authentication/validation keys secured through cryptography and thus protecting patient identity by allowing a restricted access to a particular entity in accordance with dynamic rules and policies along with strong identity validation mechanisms using blockchain configured validation devices across the integrity network. The distributed nature of the blockchain configured digital ecosystem enables shared data which provides near real-time updates across a network accessible to all authorized entities without the need for a centralized authority or exchange.

FIG. 1 illustrates generally, but not by the way of limitation, among other things, a schematic diagram depicting a communication environment 100, in which at least some embodiments herein may operate. The environment 100 provides a high-level view of one or more entities $102_{1-6}$ (hereafter entities 102 referred, in general) communicating with a multi-faceted electronic health care component 104 provided by a Social Health Record Data Bank (SHRDB) 106 over a communications network 108.

The entities 102 may include a healthcare related entity with a computing system connected to the communications network 108. Further, an "entity" is understood to mean an individual such as for whom data is managed or who manages data in the SHRDB 106. The entities 102 may include, but not limited to a patient, clinician or doctor, a research organization, a biller, a hospital, an insurance corporation, an emergency resource such as ambulance, a marketer, an advertiser, an enterprise, a sponsor, an office professional or any other individual. More generally, each entity 102 can access the multi-faceted social health care component 104 to view, control, and manage healthcare related goods or services for which a plurality of electronic health care records may be generated and deposited with the SHRDB 106.

In some embodiments, the SHRDB 106 may be centralized, for example with the use of a centralized server including in or coupled to a repository 110. In an embodiment, the SHRDB 106 may be distributed over the network 108 in the form of several distributed proxy locations as discussed later such that each such proxy location can include a similar repository. The repository 110 can store the plurality of electronic health care records including data or information related to the entities. The data can be organized in a way that facilitates local or remote information retrieval in the communication network 108 via a processing component 112. In some embodiments, the processing component 112 can be, but not limited to, a microprocessor, a microcontroller, or an equivalent mechanism. The processing component 112 may be capable of executing stored instructions to process data over the communications network 108. The data corresponding to an individual entity may or may not have been derived from medical testing or treatment (e.g., the data may have been derived from a research organization trial in which the individual voluntarily participated or data may have been derived from insurance services or any other source). More generally, "electronic health care records" may include data related to doctor's visits, lab tests, hospital stays, clinical trials, patient problems, patients health information, patient habits, patient medical history, patient appointments, patient medical insurance, patient medical bills status, or any other information.

The entities 102 may subscribe or register with the SHRDB 106 to create, view, edit, manage, and control the plurality of health care records via the multi-faceted social health care component 104. The SHRDB 120 stores the information about the entities 102 in a policy controller 114. The information described herein can be related to the role of the entities 102, preferences of the entities 102 or any other information. The policy controller 114 includes one or more rules to control an access to the multi-faceted social health care component 104 based on the roles and preferences of the entities 102. The policy controller 114 interacts with the processing component 112 to control access of the entities 102 to the electronic health care records. In an embodiment, the policy controller 114 is configured to generate an output based on the rules defined, and roles and preferences of the plurality of entities 102, upon receipt of a request from an entity such as $102_1$ for accessing the SHRDB 106. The output is a function dependent on such as the rules, roles and the preferences. In an embodiment, the processing component 112 can evaluate the value of the output. In an embodiment, the function can be subjectively defined. In another embodiment, the function can be mathematically and analytically defined such that upon receipt of values of the concerned rules, roles and the preferences corresponding to a particular entity $102_1$, the value of the function that is indicative of the output may be evaluated by the processing component 112. In such embodiments, the rules, and roles and the preferences may also be defined through a mathematical function such as based on statistical tools, scaling or rating techniques, or in the form of any other mathematical expression. The output generated either through a subjective approach or an objective or a mathematical approach may be used by the multi-faceted social health care component 104 to authorize and control access of the plurality of entities 102. In an embodiment, the multi-faceted social health care component 104 is communicatively coupled to the SHRDB 106 and adapted to be accessible by each of the plurality of entities 102 such that the multi-faceted social health care component 104 enables social interaction among the entities 102 and the SHRDB 106 over the communications network 108 for medical records transfer or sharing. The multi-faceted social health care component 104 behaves as a centralized or a distributed application and is adapted to automatically control display of the medical data or records based on the rules and the preferences.

The SHRDB 106 can be coupled to a report generator 116 that may generate health care reports and share them with the entities 102 periodically. In an embodiment, the reports can further be approved by the policy controller 114 before sharing with the plurality of entities 102.

The multi-faceted social health care component 104 may be a web-based interface displaying customized graphical interface enabling social interaction among the entities 102 over the communication network 108. The communications network 108 described herein may be the Internet. The multi-faceted social health care component 104 can be a centralized application or component or a distributed component that automatically controls display of the electronic health records based on the rules defined in the policy controller 116 of the SHRDB 106.

As described above also, in accordance with some embodiments, the entities 102 may be communicatively connected among themselves. For example, the entities 102 can interact through emailing, instant messaging, or various other modes. In some embodiments, the entities 102 can connect or interact among themselves even without going through the SHRDB 106 (thus bypassing the SHRDB 106). In some embodiments, identifiers may be used during communication among the entities 102 to enable a secured communication.

In accordance with some embodiments, the interaction of the entities 102 with the SHRDB 106 can be intermediated such that an external entity such as a different hospital, health care provider (who may be one of the entities 102 as illustrated in various figures) can operate as an intermediary among the entities 102 and the SHRDB 106. In such cases, a request such as to access the SHRDB 106 or for any other purpose may be routed via the external entity. For this, the external entity can be paid for the respective services delivered by the external entity. It must be understood that the term "external" as used herein in conjunction with defining the "external entity" is merely exemplary. However, the "external entity" can be a part of the entities 102 or may be an entity external from the group of entities 102 as illustrated in various figures.

In accordance with some embodiments, the interaction of the entities 102 with the SHRDB 106 can be non-intermediated such that no external entity such as a different hospital, health care provider, and the like operates as an intermediary between the entities 102 and the SHRDB 106. In such cases, the entities 102 can directly communicate with the SHRDB 106.

In accordance with some embodiments, the mode of interaction of the entities 102 with the SHRDB 106 can be of the type of "directed" in which an external entity similar to the external entity described above may provide a directed care to the entities. In such cases, the external entity can be paid for the directed care that it provides to the entities 102. In case of a directed type of interaction, the external entity may provide directed care, or may provide instructions to the entities 102, or monitor instructions being followed by the entities 102, or generate reports and share them with the entities 102, and the like.

In some embodiments, the interaction of the entities 102 with the SHRDB 106 can be of the type of "undirected" in which no external entity similar to the external entity described above is involved to provide a directed care.

In some embodiments, the mode of operation and interaction can be purely intermediated, purely non-intermediated (also referred to as disintermediated interchangeably), purely directed, purely undirected, or a combination thereof. In some embodiments, the mode of interaction may be customized for each of the entities 102. For example, an entity such as entity $102_1$ may receive an intermediated care while entity $102_2$ may receive a non-intermediated care.

In an embodiment, the plurality of entities 102 may include a first entity $102_1$, a second entity $102_2$, a third entity $102_3$, a fourth entity $102_4$, and a fifth entity $102_5$. In an aspect, the first entity $102_1$ receives a purely intermediated care from the SHRDB 106 or in combination with a third party. The second entity $102_2$ receives a purely non-intermediated care from the SHRDB 106 or in combination with the third party. The third entity $102_3$ receives a purely directed care from the SHRDB 106 or in combination with the third party. The fourth entity $102_4$ receives a purely undirected care from the SHRDB 106 or in combination with the third party. The fifth entity $102_5$ receives a customized service with a combination of two or more of the intermediated, non-intermediated, directed, and undirected care from the SHRDB 106 or in combination with the third party.

In an embodiment, the multi-faceted social health care component 104 is adapted to interact with the first entity $102_1$ of the plurality of entities 102 such that the first entity $102_1$ receives a purely intermediated care from the SHRDB 106 or in combination with a third party, the second entity $102_2$ of the plurality of entities 102 such that the second entity $102_2$ receives a purely non-intermediated care from the SHRDB or in combination with a third party, the third entity $102_3$ of the plurality of entities 102 such that the third entity $102_3$ receives a purely directed care from the SHRDB 106 or in combination with a third party, a fourth entity $102_4$ of the plurality of entities 102 such that the fourth entity $102_4$ receives a purely undirected care from the SHRDB 106 or in combination with a third party, the fifth entity $102_5$ of the plurality of entities 102 such that the fifth entity $102_5$ receives a combination of two or more of the intermediated, non-intermediated, directed, and undirected care from the SHRDB 106 or in combination with a third party.

In an embodiment, the multi-faceted social health care component 104 is configured to identify at least one source location and a target location upon receipt of a request from an entity such as $102_1$. The source location is defined as at least a portion of the medical records that is requested by an entity $102_1$ that sends a request to the SHRDB 106 to such as view or receive at least a portion of the medical records or allow another entity such as $102_2$ or any other entity to view or receive the at least a portion of the medical records. In other words, the source location specifies at least a portion of the medical records. The target location or the target location entity is defined as an entity that is authorized by the request sending entity through the request to view or receive at least the portion of the medical records (that is the source location). The target location entity such as $102_2$ thus serves as a recipient entity of the at least a portion of the medical records or the source location. The target location $102_2$ may be identified by such as one or more of (a) an explicit or implicit permission from an owner of the source location such as an owner of the at least a portion of the medical records such as $102_1$, (b) an indication of the extent of sharing that is the extent and nature of the medical records or the source location, (c) a nature and characteristic of the target location $102_2$, (d) a purpose of the sharing of the medical records to the target location $102_2$, and (e) a timeframe for allowance of sharing of the at least a portion of the medical records. In an aspect, for example, the request sending entity $102_1$ may define a specific name and identifier of the target location entity $102_2$ in the request such as through an implicit or explicit permission from the owner $102_1$ of the source location such as the owner $102_1$ of the at least a portion of the medical records and thus the target location $102_2$ can be identified and defined from the request. In an aspect, the owner entity $102_1$ may send the request including a rule or may predefine a rule providing details about the entities who can be allowed to access a defined portion of the medical records and to a defined extent. The owner entity $102_1$ can in such case define such as an indication of the extent of sharing that may vary for different target entities. The target location $102_2$ can thus be defined or identified by the SHRDB 106. In an aspect, the owner entity $102_1$ may define a rule for sharing of the at least a portion of the medical records such as based on the nature and characteristics of the target location $102_2$. For example, a particular owner $102_1$ of the at least a portion of the medical records may define a rule such that only hospitals can access a defined portion of the medical records, while any research institute may no access, and the like. In another aspect, the purpose of the sharing may also govern the identification of the target location $102_2$ for example an owner entity such as $102_1$ may define that a particular portion of the medical records may be accessed only for the purpose of nursing and surgical care, and not for research purposes, and the like. In another aspect, the target location $102_2$ may be defined based on a timeframe for allowance of sharing of the medical records. For example, an owner entity $102_1$ may allow a particular target location $102_2$, through such as the request or by predefining, to access the at least a portion of the medical records for a predefined period of time only. In some embodiments, only one of the (a) to (e) may govern identification of the target location $102_2$. In an embodiment, more than one of the (a) to (e) may govern selection or identification of the target location $102_2$. In an embodiment, the parameters (a) to (e) may be defined mathematically through a mathematical function and statistical tools such that that any target location such as $102_2$ may be evaluated for various variables based on the parameters (a) to (e) to determine a cumulative effect numerical value for assessing the level of sharing of the medical records, if any. The function considering the impact of the (a) to (e) may be evaluated by such as the processing component 112. In an embodiment, the target location $102_2$ is automatically determined based on one or more of (a) to (e) upon receipt of the request from the owner entity $102_1$ or is predefined within the SHRDB 106 by the owner entity $102_1$.

In an embodiment, in addition to or alternatively, the source location may also be defined based on and may be dependent on such as the parameters (a) to (e) or any other parameter.

In an embodiment, the sharing of the at least a portion of the medical records with the target location $102_2$ may include providing viewing rights to the target location $102_2$. In this embodiment, the SHRDB 106 may be configured to allow partial viewing of the medical records corresponding to the owner entity $102_1$ by the target location $102_2$ based on the one or more of (a) to (e), and based on the request from the owner entity $102_1$ or based on predefined rules by the owner entity $102_1$. In an embodiment, the SHRDB 106 may be configured to stop any viewing or select which parts to be viewed by the target location $102_2$ based on the one or more of (a) to (e) and based on the request from the owner entity $102_1$ or based on predefined rules by the owner entity $102_1$. In an embodiment, the SHRDB 106 may be configured to determine or facilitate the owner entity $102_1$ of the medical records to determine who has viewed the medical records. Based on knowing who has viewed the medical records, the owner entity $102_1$ may redefine or may be facilitated by the SHRDB 106 to accordingly redefine the one or more of the (a) to (e). The owner entity $102_1$ may also accordingly make a decision or may be facilitated by the SHRDB 106 to make a decision about the partial viewing of the medical records (that is the source location) corresponding to the owner entity $102_1$ by the target location $102_2$ based on the redefined one or more of (a) to (e). In an embodiment, the owner entity $102_1$ may also accordingly make a decision or may be facilitated by the SHRDB 106 to make a decision about the stopping of any viewing or selecting which parts to be viewed of the medical records (that is the source location) corresponding to the owner entity $102_1$ by the target location $102_2$ based on the redefined one or more of (a) to (e).

In an embodiment, the social health care component 104 of the SHRDB 106 is configured to identify who has viewed the medical records in real time and share information about who has viewed the medical records with the owner $102_1$ in real time, such that the owner $102_1$ allows fully or partially or stops viewing of the medical records by the target location $102_2$ in real time. In an embodiment, the allowance or denial by the owner $102_1$ can be performed manually such as without predefining rules and guidelines for allowance and denial. In accordance with such embodiments, the owner entity $102_1$ can be facilitated to control viewing rights of the at least a portion of the medical records on it owns without predefining any rules. For example, the owner $102_1$ may initially allow access to any of the plurality of entities 102 and then receive information from the SHRDB 106 about who has viewed the medical records. Based on who has viewed the medical records and further information about who has viewed the medical records and also the purpose of viewing of the medical records, the owner entity $102_1$ may decide as to whether the owner entity $102_1$ should allow at least partial viewing of the at least a portion of the medical records by other entities such as $102_2$ or stop viewing. This may be decided in association with such as the parameters (a) to (e).

In an embodiment, during the time of initial accessing of the at least a portion of the medical records and the time the owner entity $102_1$ decides whether to allow viewing or stop viewing the medical records by the entities, the owner entity $102_1$ may be facilitated by the SHRDB 106 to allow other entities to view a portion of the at least a portion of the medical records as defined by the owner entity $102_1$ referred to as 'no objection segment' of the at least a portion of the medical records. The 'no-objection' segment for example may refer to some non-confidential or superficial details of the medical records, in an embodiment, and not any detailed or confidential data. In an embodiment, the 'no-objection' segment of the medical records can be allowed to be viewed by the entities such as $102_2$ for a defined period of time after initiation of viewing by the entities. In an aspect, if the owner entity $102_1$ decides about allowance or denial of further viewing of the medical records in addition to the 'no-objection' segment in a time that is less than the defined time for the 'no-objection' segment viewing, then the decision of allowance or denial can be implemented to either allow further viewing by the entities beyond the 'no-objection' segment in case of allowance, or stop further viewing in case of denial, or allow to view only the 'no-objection' segment. In such embodiments where the time to allow or deny the viewing beyond the 'no-objection segment' is less than the defined time, then the 'no-objection' segment viewing may be converted to viewing as decided or authorized by the owner $102_1$. If the time to allow or deny the viewing beyond 'no-objection' segment is more than the defined time then the 'no-objection' segment viewing time may be extended by the owner $102_1$ by allowing more of medical records under 'no objection' to be viewed or repeating a previously viewed 'no-objection' segment of the medical records. The defined time associated with the 'no-objection' viewing and the portion of the medical records corresponding to the 'no objection' viewing may be further defined by the owner entity $102_1$ automatically or manually based on one or more of the parameters (a) to (e) or any other parameter.

The connections connecting the various entities 102 as shown in FIG. 1 are merely to illustrate the possibility of the entities 102 to interact among themselves. This should not be considered to limit the entities 102 to be located at a single place or directly connected. A direct connection or singly located may not necessarily be true, however possible. The entities 102 may still be located remotely and communicate through wired mode or wireless mode.

In some embodiments, the multi-faceted social health care component 104 may also be referred to as a multi-faceted electronic health care component. Similarly, the SHRDB 106 may also be referred to as EHRDB (Electronic Health Record Databank). In some embodiments, the SHRDB 106, the multi-faceted social healthcare component 104, and various other components illustrated in FIG. 1 may be blockchain configured and the communication network 108 may be a social integrity network as discussed in conjunction with various figures later without limitations.

The entities 102 may be associated with a plurality of social aware networks 118, a plurality of environment and other sensors 120, a plurality of wearable health monitoring devices 122, a plurality of scanners 124, a plurality of Global Positioning System-based devices 126 for generating and extracting the medical records that go into the SHRDB 106. These components are further discussed in conjunction with FIG. 6.

Figure 2:
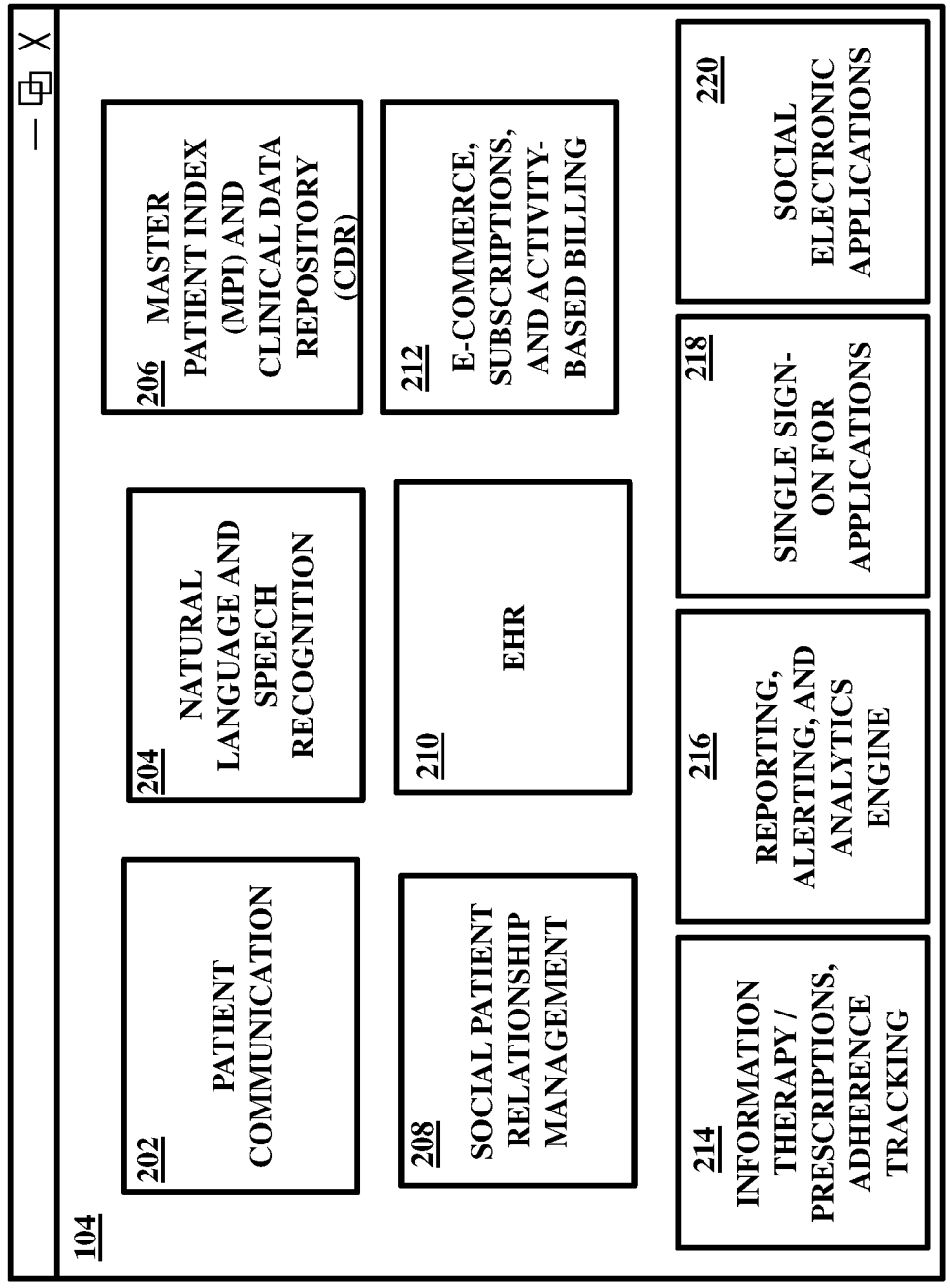
FIG. 2 illustrates generally, but not by the way of limitation, among other things, an example of an interactive social users interface display of a multi-faceted social health care component, in accordance with embodiments herein.

FIG. 2, with reference to FIG. 1, illustrates generally, but not by the way of limitation, among other things, examples of an interactive social user interface 200 of the multi-faceted social health care component 104. The multi-faceted social health care component 104 may communicate with the SHRDB 106 to provide information related to the entities 102. The interface 200 provides display of different modules 202-220 to different entities 102, such that a social cloud among the different entities 102 may be formed to actively interact with each other via the multi-faceted social health care component 104. Restricted access and display of these modules 202-220 may be provided to the entities 102 based on their specific roles and policies implemented by the SHRDB 106 for respective entities 102.

Modules 202-218 may provide different features and information to the entities 102. In some embodiments, module 202 which is patient communication may facilitate the entities 102 to socially communicate with each other. For example, module 202 may provide active social communication among the entities 102 via SMS, Instant Messaging (IM), Email, Voice communication, Video conferencing and the like modes. Module 202 may provide different ways and options to the entities 102 for active social communication, such that a social cloud or platform may be implemented to communicate among the different entities 102. In some embodiments, the multi-faceted social health care component 104 may facilitate the entities 102 to actively interact with each other via a natural language and/or speech recognition techniques via module 204. Module 206 may provide the entities 102, particularly the entities such as doctors and research organizations with master patient index and clinical data repositories such that the entities 102 may view and use the information related to different patients.

The multi-faceted social health care component 104 includes a module 208 that deploys or employs social entity (such as a patient) relationship management techniques that may help in building long-term relationships, such that the entities 102 specifically clinicians can establish ongoing relationships with their patients. Module 210 may display health records such as electronic health records of the entities 102. In accordance with various embodiments, module 210 can provide different types of information to the entities 102 based on their specific roles and policies.

The multi-faceted social health care component 104 may also include a module 212 for performing secure electronic transactions. Module 212 may facilitate the entities 102 to pay their medical bills, or purchase any health related products. With the use of a module 214, the multi-faceted social health care component 104 may keep a track of therapies and medical prescription of different patients and constantly display the tracked information to the doctors, clinicians or other entities via module 214. The multi-faceted social health care component 104 may allow the entities 102 to generate reports of the electronic health information or any other information via module 216. Module 216 may also display alerts defined from the electronic health information of the entities 102. Module 216 may also deploy analytics processing techniques for analyzing patient information to generate reports and charts.

The multi-faceted social health care component 104 also includes a module 218 to provide a single sign-on interface for a plurality of and different social electronic applications 220 such as Gmail™, Yahoo™, Facebook™, Twitter™ and the like. The SHRDB 106 integrates the entities 102 with social electronic applications 220 and may provide single sign on feature to the entities 102, such that the entities 102 can interact with the multi-faceted social health care component 104 via the social electronic applications 220.

The above described modules 202-218 are not described by the way of limitation but merely for exemplary purposes for some embodiments herein. In accordance with various other configurations, many such or other types of modules can be integrated within the embodiments herein. The interface 200 of the multi-faceted social health care component 104 may be customized to display the above described modules based on the entities role and policies defined by the SHRDB 106.

Figure 3A:
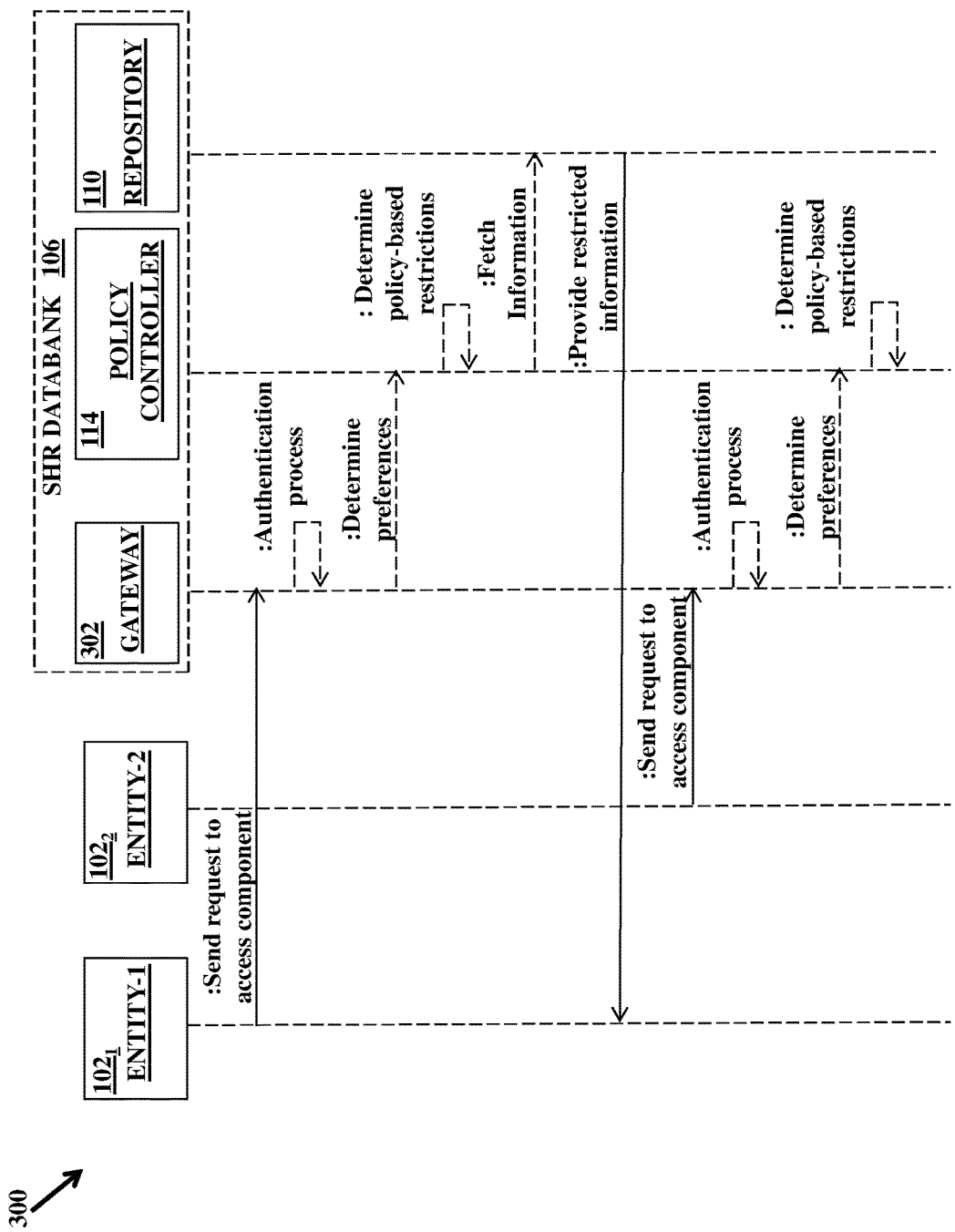
FIGS. 3A and 3B illustrate generally, but not by the way of limitation, a sequence diagram depicting a method for restricting access to the multi-faceted social health care component based on the determined policy-based restrictions, in accordance with embodiments herein.
Figure 3B:
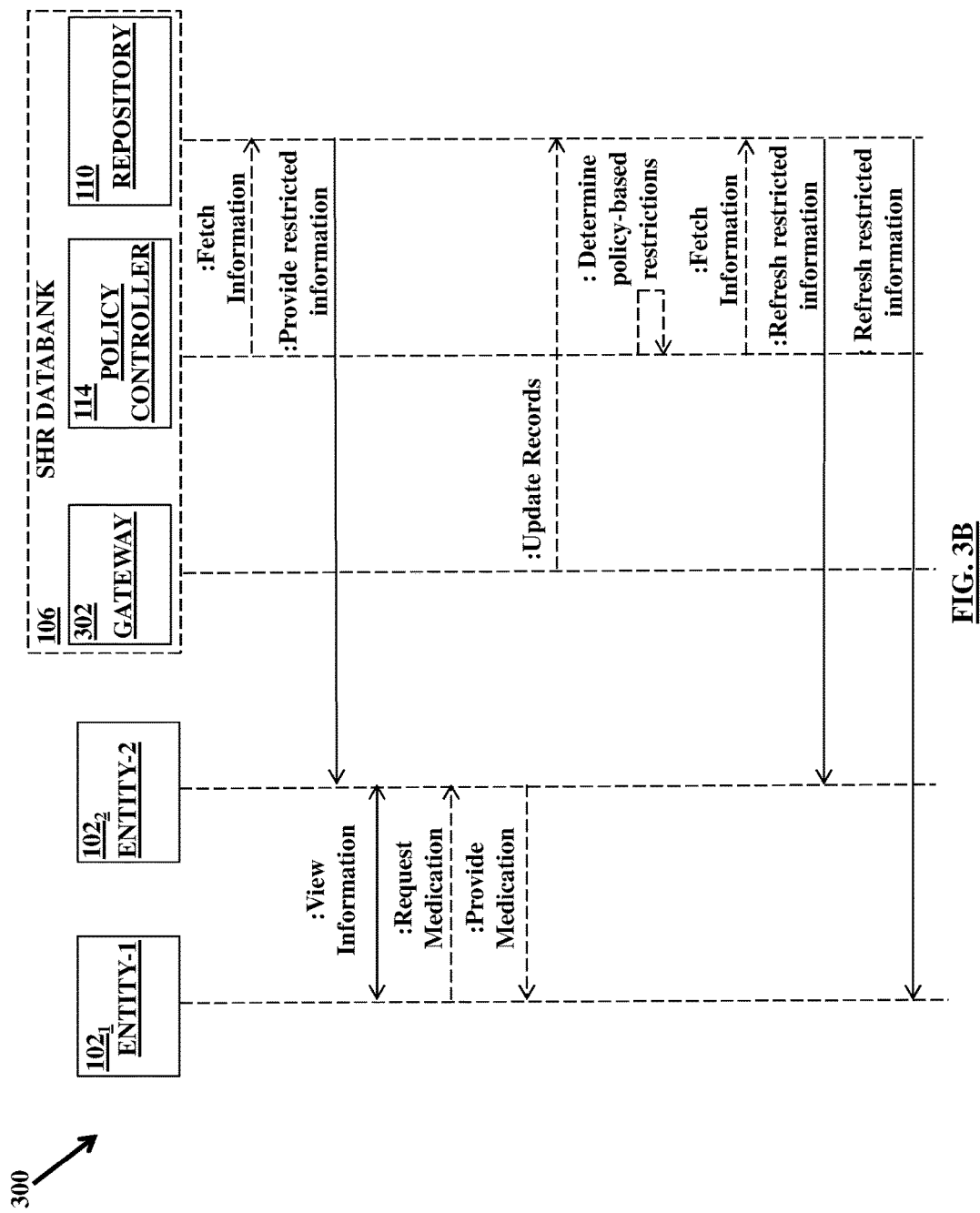

FIGS. 3A and 3B, with reference to FIGS. 1 and 2, illustrate generally, but not by the way of limitation, a sequence diagram depicting an example of a method 300 for defining access to policy-controlled portions of the multi-faceted social health care component 104. In various embodiments, the multi-faceted social health care component 104 can facilitate the entities 102 to socially interact with one another.

The entities 102 may use the communication network 108 to access the multi-faceted social health care component 104. The multi-faceted social health care component 104 may provide access to the SHRDB 106 to allow the entities 102 to socially interact with the SHRDB 106. For example, an entity such as entity 102₁ may send a request to access the multi-faceted social health care component 104. The SHRDB 106 may allow entity 102₁ to access the multi-faceted social health care component 104 via a gateway 302 such as a web page. The gateway 302 may restrict and/or grant access to the multi-faceted social health care component 104 based on the account information such as user name and password of entity 102₁. For example, the page may prompt entity 102₁ connecting to the multi-faceted social health care component 104 for a user name and a password if the gateway 302 is an internet page.

In some embodiments, the SHRDB 106 may authenticate entity 102₁ based on a defined criterion. Once authenticated, the SHRDB 106 may use the policy controller 114 to determine the role and preferences of entity 102₁ The policy controller 114 may determine restrictions to the portions such as various modules of the multi-faceted social health care component 104 (as described above) based on stored preferences related to the role of entity 102₁. The SHRDB 106 may send a request to retrieve information from the repository 110. The SHRDB 106 may also customize the interface 200 of the multi-faceted social health care component 104 in accordance with the various policies related to the role of entity 102₁. The SHRDB 106 may customize the interface 200 of the multi-faceted social health care component 104 in accordance with the determined policy-based restrictions/access related to entity 102₁.

In some embodiments, another entity such as entity 102₂ may also access the multi-faceted social health care component 104, such that entity 102₁ and entity 102₂ may interact with each other also. The SHRDB 106 can allow entity 102₁ and entity 102₂ to view the information of each other and interact with each other via the multi-faceted social health care component 104, which may result in forming the social cloud among the entities 102₁ and 102₂. The above description is provided with an example with respect to entity 102₁ and entity 102₂. Similarly, various other entities 102 may also interact among themselves.

Figure 4:
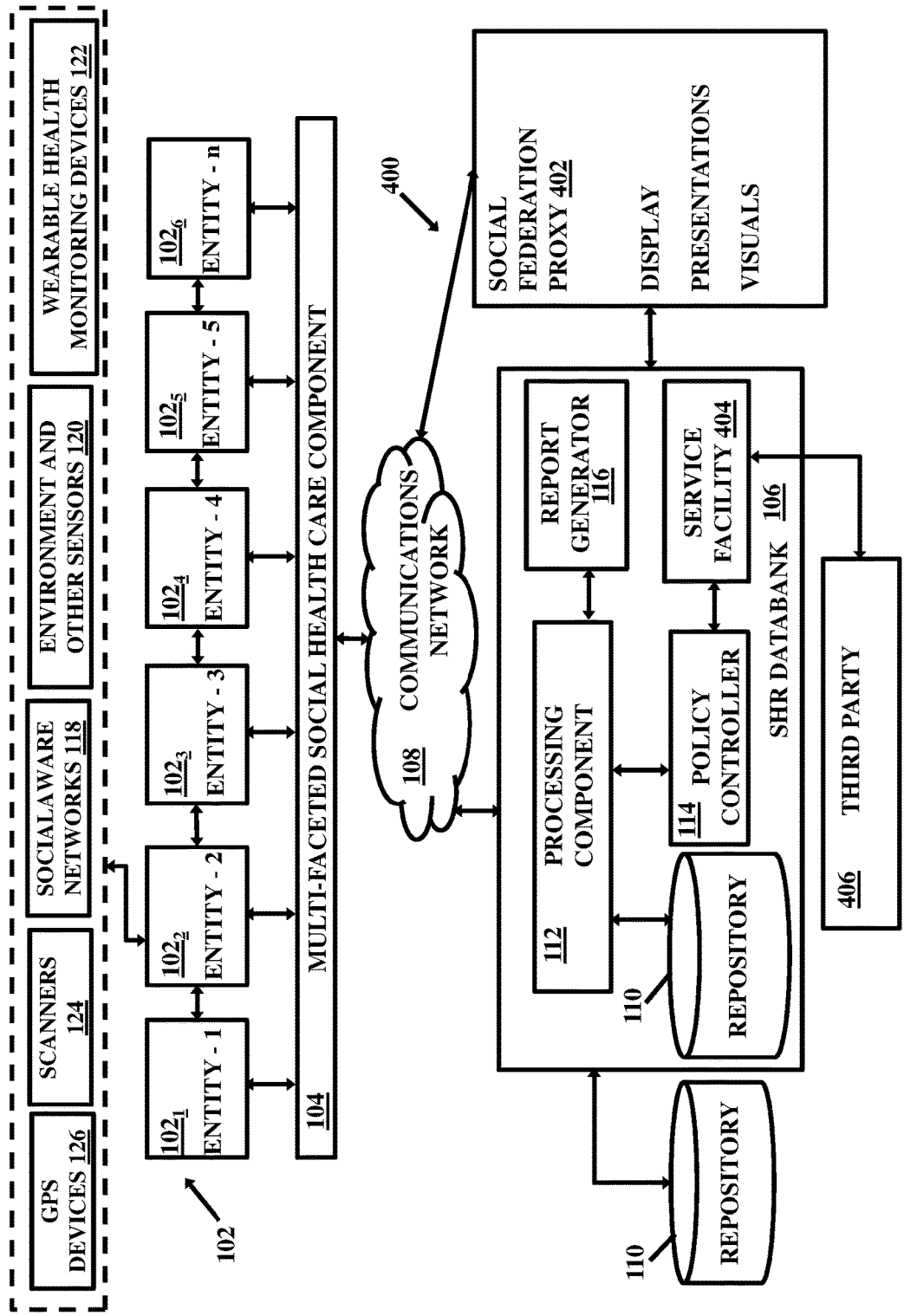
FIG. 4 illustrates generally, but not by the way of limitation, among other things, a schematic diagram depicting a communications environment, in which some embodiments herein may operate.

FIG. 4, with reference to FIGS. 1 through 3B, illustrates generally, but not by the way of limitation, among other things, a schematic diagram depicting a communication environment 400, in which at least some embodiments herein may operate. The environment 400 provides a high-level view of the one or more entities 102 communicating with the multi-faceted electronic health care component 104 provided by the Social Health Record Data Bank (SHRDB) 106 over the communications network 108 in an embodiment. In accordance with the embodiment illustrated in FIG. 4, a social federation proxy 402 is coupled to the SHRDB 106 or a server hosting the SHRDB 106. The social federation proxy 402 is configured to retrieve relevant portions of the medical records or social records from the SHRDB 106 associated with an entity such as entity 102₁ upon a request from entity 102₁. While the SHRDB 106 is configured to store and manage the social records corresponding to the plurality of entities 102, the social federation proxy 402 may or may not store the social records. In an embodiment, the social federation proxy 402 may provide a virtual view of the storage to the entities 102. In an embodiment, the social federation proxy 402, upon retrieval of the social records from the SHRDB 106, can display or present them to the entities 102 upon request from the entities 102 such that the viewers get a feel as if they are viewing or accessing the SHRDB 106 directly. With this implementation, the social federation proxy 402 may not behave as a storage facility, instead, provides a virtual platform for the entities 102 to such as view the displayed or presented social records as requested by them through such as displays, presentations, visuals, graphics, and the like and also edit or manage the records. In an embodiment, however, the social federation proxy 402 may store the records actually so that multiple copies of the records can be located at different locations. The social federation proxy 402 may pull the social records from the SHRDB 106 for presentation, display, and the like either permanently or only when accessed instead of permanent storage. In case the records are not stored at the social federation proxy 402, it can maintain references to the records stored in the SHRDB 106 so that upon access by the entities 102, the records can be fetched from the SHRDB 106.

In an embodiment, the social federation proxy 402 allows the two-way communication between the entities 102 and the SHRDB 106. For example, the SHRDB 106 can collect the social records from several social aware networks or applications 118 such as through the entities 102 that are associated with the several social aware networks or the applications 118. The social records can be obtained from other sources such as various devices and sensors as discussed above and further elaborated in conjunction with subsequent figures. The collected social records can be stored in a physical storage of the SHRDB 106. The social records thus stored in the SHRDB 106 can further be retrieved by the entities 102 and thus distributed across the various social aware networks or the applications 118 through the social federation proxy 402. The entities 102 can enjoy the facility of integration, distribution and retrieval of the social records all at the same time without even knowing that the access is or the social records are routed through two different levels—social federation proxy 402 and the SHRDB 106. In some embodiments, a virtualization layer may be provided to create a virtual environment that is capable of allowing the entities 102 to share their social records from the social aware networks or the applications 118 and also view or retrieve the social records from the social federation proxy 402 hiding the difference between the social federation proxy 402 and the SHRDB 106 from the entities 102. FIG. 4 illustrates only one social federation proxy 402; however, multiple such social federation proxies may be employed to provide a distributed architecture.

In an embodiment, a service facility 404 may be provided with the SHRDB 106. The service facility 404 may be configured to provide various services such as intermediated care, non-intermediated care, directed care, undirected care, and custom care to the entities 102. The services can be provided by the SHRDB 106 directly. In another embodiment, the SHRDB 106 can be connected to a third party 406 such as to provide the various services either through or in combination with the third party 406.

Figure 5:
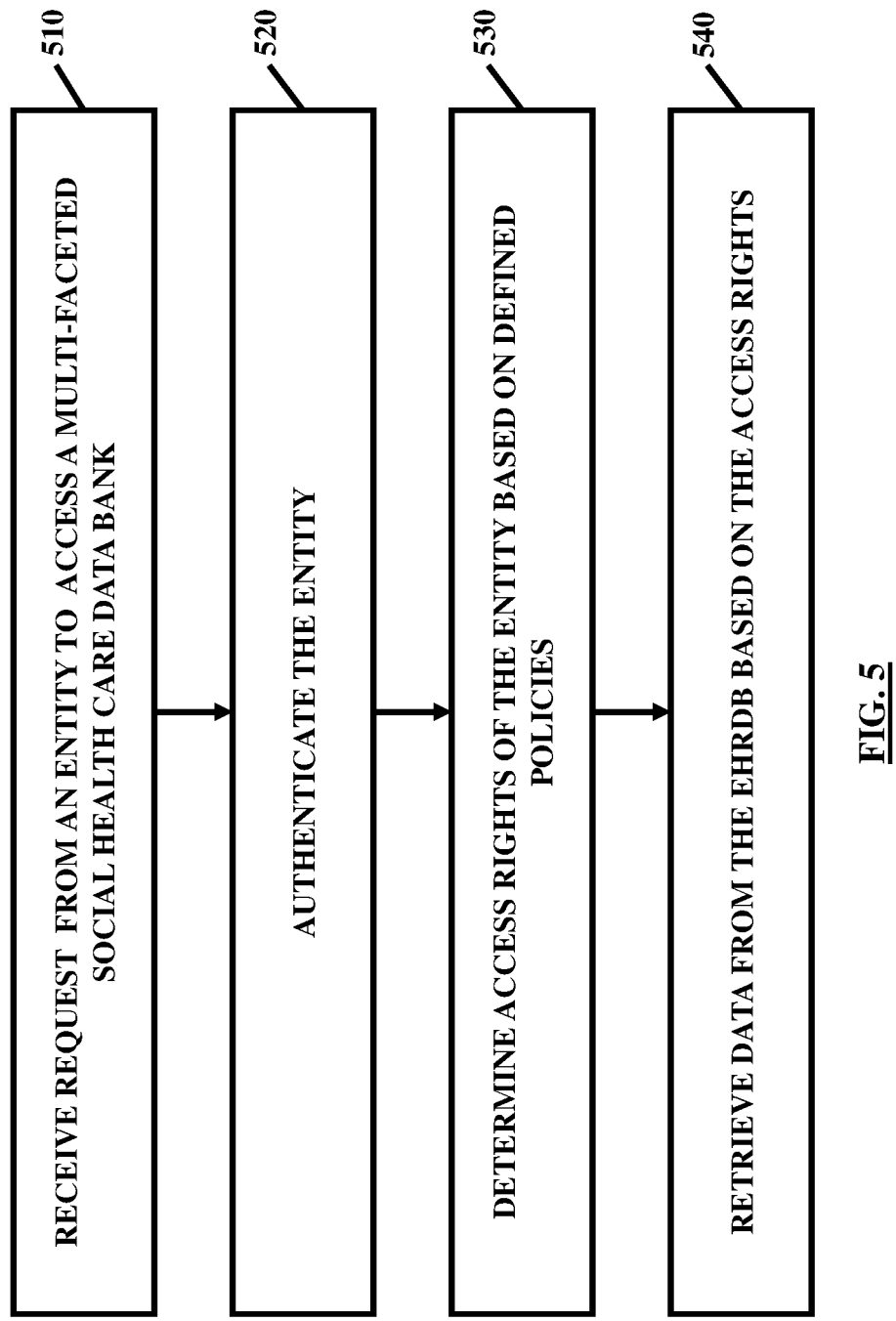
FIG. 5 illustrates a method flowchart for accessing a social health care component by an entity, in accordance with embodiments herein.

FIG. 5, with reference to FIGS. 1 through 4, illustrates a method flowchart for accessing the SHRDB 106 by an entity such as entity $102_1$. At step 510, the SHRDB 106 receives a request from entity $102_1$ for accessing the multi-faceted SHRDB 106. At step 520, the SHRDB 106 or the processing component 112 may authenticate entity $102_1$. Once authenticated, the SHRDB 106 determines access right of entity $102_1$ based on defined policies, rules and preferences such as those identified by the SHRDB 106 or pre-stored in the policy controller 114, at step 530. In some embodiments, the SHRDB 106 may retrieve the medical records from the repository as requested in the request of entity $102_1$, at step 540. The step of retrieving of the medical records may include at least one of sharing of the medical records either partially or fully to entity $102_1$ or to any other entity $102_2$ of the plurality of entities 102 as suggested or authorized by the owner entity $102_1$ and allowing viewing of the medical records at least partially by entity $102_1$ or $102_2$.

In an embodiment, the method may include retrieving the social records, collected by the SHRDB 106 from several distinct locations such as distinct social aware networks or applications 118, by the social federation proxy 402 such as for displaying or presenting the social records to the entities 102. In an embodiment, the method allows the two-way communication between the entities and the SHRDB 106 with the use of the social federation proxy 402. For example, the SHRDB can collect the social records from several social aware networks or applications 118 such as through the entities 102 that are associated with the several social aware networks or the applications 118. The collected social records can be stored in a physical storage of the SHRDB 106. The social records thus stored in the SHRDB 106 can further be retrieved by the entities 102 and thus distributed across the various social aware networks or the applications 118 through the social federation proxy 402.

In some embodiments, the method may also include determining a type of service to be provided to entity $102_1$ or $102_2$ such as a service involving pure intermediated care, pure non-intermediated care, directed care, undirected care or a combination thereof as discussed above. Accordingly, the determined type of service may be initiated and provided to entity $102_1$ by the SHRDB 106 or in combination with third parties 406.

In an embodiment, the request from entity $102_1$ may further include an instruction to share at least a portion of the medical records to entity $102_1$ or the target location entity $102_2$. In case of sharing with an entity other than the owner entity $102_1$ such as entity $102_2$, the method may include sharing the at least a portion of the medical records based on at least one of (a) an explicit or implicit permission from entity $102_1$, (b) an indication of the extent of sharing, (c) a nature and characteristic of the target location entity $102_2$, (d) a purpose of the sharing of the medical records to the target location entity $102_2$, and (e) a timeframe for allowance of sharing of the medical records. In an embodiment, the step of sharing of the medical records with the target location $102_2$ may include providing viewing rights to the target location $102_2$ such that the method allows partial viewing of the at least a portion of the medical records by the target location $102_2$ based on the one or more of (a) to (e) or stop any viewing or select which parts to view based on the one or more of (a) to (e), or determine or facilitate entity $102_1$ to determine who has viewed the medical records. In an embodiment, the method may include redefining the one or more of the (a) to (e). The method may include making a decision about the partial viewing of the at least a portion of the medical records by the target location entity $102_2$ Based on the one or more of (a) to (e) and the stopping of any viewing and selecting which parts to view based on the one or more of (a) to (e). Though parameters such as (a) to (e) are defined herein but it must be appreciated that other parameters may also be defined and considered without limitations.

Figure 6:
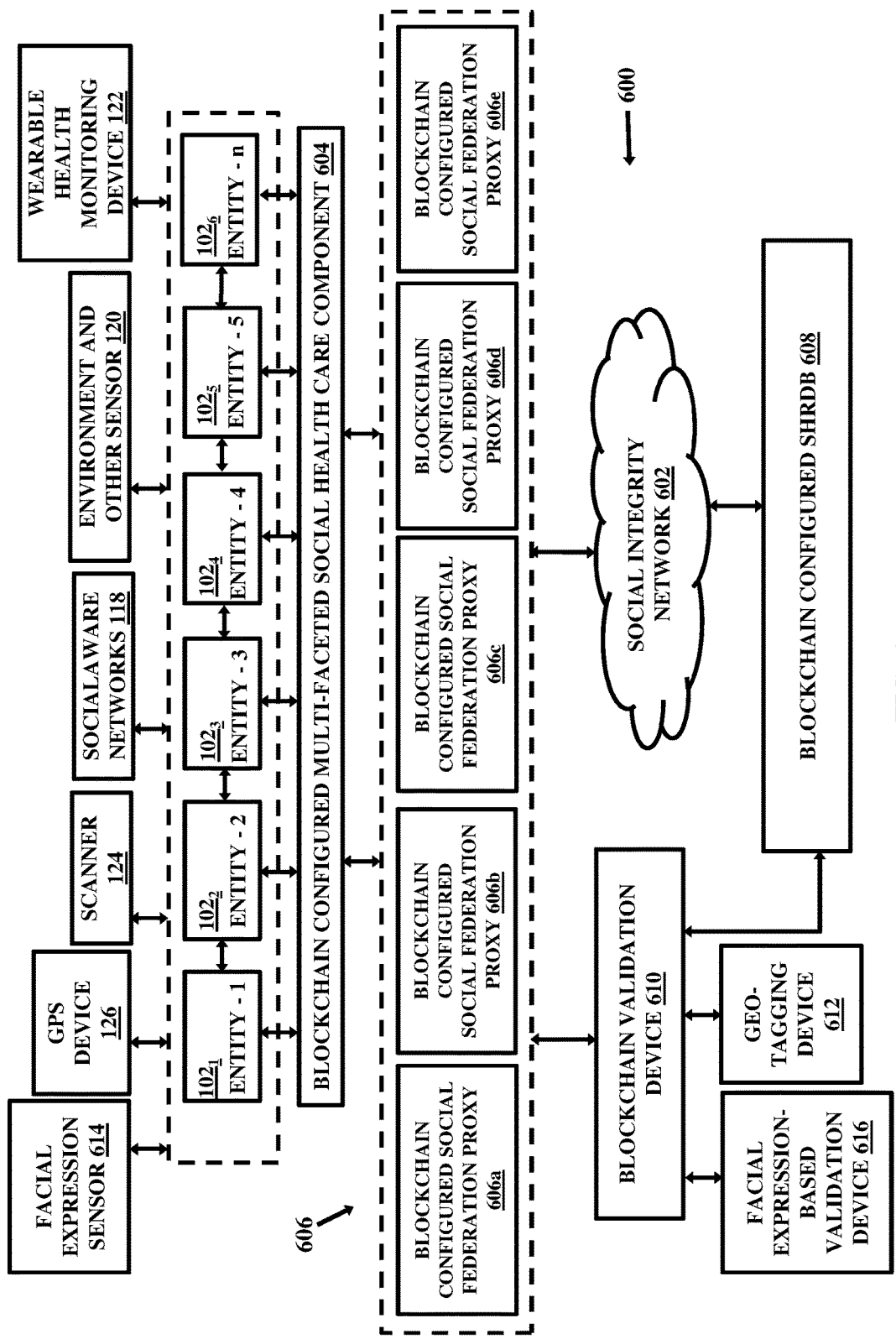
FIG. 6 illustrates a device-driven non-intermediated blockchain configured digital ecosystem in a social integration network, in accordance with embodiments herein.

FIG. 6, with reference to FIGS. 1 through 5, illustrates a device-driven non-intermediated blockchain configured digital ecosystem 600 in a social integrity network 602. As shown, the various entities 102 may access a blockchain configured multi-faceted social healthcare component 604 to interact with a plurality of blockchain configured social federation proxies 606a, 606b, 606c, 606d, and 606e (together referred to as 606). The blockchain configured social federation proxies 606 may be communicatively linked with a blockchain configured social health record databank 608 to provide a distributed access across the entire social integrity network 602 for the entities 102.

The entities 102 can access the blockchain configured multi-faceted social health care component 602 to view, control, and manage healthcare records which may be aggregated from a variety of healthcare information sources. The entities 102 may represent patients, clinicians, physicians, diagnostic centers, care takers, care providers, financial institutes engaged in health insurance, taxation etc, and the like as discussed earlier in conjunction with various figures without limitations. The entities 102, in an embodiment, may represent computing systems associated with patients, clinicians, physicians, diagnostic centers, care takers, care providers, financial institutes engaged in health insurance, taxation etc, and the like.

The blockchain configured multi-faceted social health care component 602 is configured to allow collaboration and interaction among the entities 102 through the blockchain configured Social Health Record Data Bank (SHRDB) 708 and the blockchain configured social federation proxy 606. The blockchain configured SHRDB 608 can be configured to provide a repository similar to the repository 110 for the storage of data such as the healthcare records generated by the entities 102. The various portions of the multi-faceted social health care component 602 can be accessed by the entities 102 based on entity specific preferences and roles as discussed earlier in conjunction with various figures.

In some embodiments, the blockchain configured SHRDB 608, described herein, may be distributed in the form of blockchain configured social federation proxy 606 to serve as disintermediated blocks of the blockchain configured SHRDB 608. The blockchain configured SHRDB 608 and the social federation proxy 606 can store the electronic health records including data or information related to the entities 102 and data coming from various information sources associated with the entities 102. The data can be organized in a way that facilitates local or remote information retrieval in the social integrity network 602 via a processing component similar to the processing component 112. The processing component 112 has been described in conjunction with FIG. 1 already.

The entities 102 may subscribe or register with the blockchain configured SHRDB 608 to create, view, edit, manage, and control the health records via the blockchain configured multi-faceted social health care component 602. The blockchain configured SHRDB 608 stores the information about the entities 102 in a policy controller which may be similar to the policy controller 114. The information described herein can be related to the role of the entities 102, preferences of the entities 102 or any other information. The policy controller 114 may include one or more rules to control an access to the blockchain configured multi-faceted social health care component 602 based on the roles and preferences of the entities 102. The policy controller 114 interacts with the processing component 112 to control access of the entities 102 to the health records. In an embodiment, the policy controller 114 is configured to generate an output based on the rules defined, and roles and preferences of the plurality of entities 102, upon receipt of a request from an entity such as $102_1$ for accessing the blockchain configured SHRDB 608. The output is a function dependent on such as the rules, roles and the preferences. In an embodiment, the processing component 112 can evaluate the value of the output. In an embodiment, the function can be subjectively defined. In another embodiment, the function can be mathematically and analytically defined such that upon receipt of values of the concerned rules, roles and the preferences corresponding to a particular entity $102_1$, the value of the function that is indicative of the output may be evaluated by the processing component 112. In such embodiments, the rules, and roles and the preferences may also be defined through a mathematical function such as based on statistical tools, scaling or rating techniques, or in the form of any other mathematical expression. The output generated either through a subjective approach or an objective or a mathematical approach may be used by the blockchain configured multi-faceted social health care component 602 to authorize and control access of the plurality of entities 102. In an embodiment, the multi-faceted social health care component 602 is communicatively coupled to the blockchain configured SHRDB 608 and the blockchain configured social federation proxy 606 and adapted to be accessible by each of the plurality of entities 102 such that the blockchain configured multi-faceted social health care component 602 enables social interaction among the entities 102 and the blockchain configured SHRDB 608 over the social integrity network 602 for medical records transfer or sharing or editing. The blockchain configured multi-faceted social health care component 602 behaves as a distributed blockchain dependent application and is adapted to automatically control display of the medical data or records based on the rules and the preferences.

The blockchain configured SHRDB 608 can be coupled to a report generator similar to the report generator 116 that may generate health care reports and share them with the entities 102 periodically. In an embodiment, the reports can further be approved by the policy controller before sharing with the plurality of entities 102.

The blockchain configured multi-faceted social health care component 602 may be a web-based interface displaying customized graphical interface enabling social interaction among the entities 102 over the social integrity network 602 in a distributed manner. The social integrity network 602 described herein may be enabled through the Internet. The blockchain configured multi-faceted social health care component 604 can be a distributed blockchain type application or component that automatically controls display of the electronic health records based on the rules defined in the policy controller 114 of the blockchain configured SHRDB 608.

In an embodiment, the blockchain configured multi-faceted social health care component 604 may be configured to identify the at least one source location and the target location upon receipt of a request from an entity such as $102_1$ in a manner as described in conjunction with various figures particular FIG. 1. The source location and the target location also have been defined in conjunction with FIG. 1. The rules and mechanics defining identification and/or access and/or viewing of the source location or medical records by the entities 102 or the target location may be same as those described in conjunction with FIG. 1 without limitations. For example, in an embodiment, more than one of the (a) to (e) may govern selection or identification of the target location such as $102_2$. In an embodiment, the parameters (a) to (e) may be defined mathematically through a mathematical function and statistical tools such that that any target location such as $102_2$ may be evaluated for various variables based on the parameters (a) to (e) to determine a cumulative effect numerical value for assessing the level of sharing of the medical records, if any. Various other embodiments have already been discussed in conjunction with FIG. 1 and other figures.

In an embodiment, the blockchain configured social health care component 604 of the blockchain configured SHRDB 608 is configured to identify who has viewed the medical records in real time and share information about who has viewed the medical records with the owner $102_1$ in real time, such that the owner $102_1$ allows fully or partially or stops viewing of the medical records by the target location $102_2$ in real time. In an embodiment, the allowance or denial by the owner $102_1$ is performed manually such as without predefining rules and guidelines for allowance and denial. In accordance with such embodiments, the owner entity $102_1$ can be facilitated to control viewing rights of the at least a portion of the medical records it owns without predefining any rules. For example, the owner $102_1$ may initially allow access to any of the plurality of entities 102 and then receive information from the blockchain configured SHRDB 608 about who has viewed the medical records. Based on who has viewed the medical records and further information about who has viewed the medical records and also the purpose of viewing of the medical records, the owner entity $102_1$ may decide as to whether the owner entity $102_1$ should allow at least partial viewing of the at least a portion of the medical records by other entities such as $102_2$ or stop viewing. This may be decided in association with such as the parameters (a) to (e). This has been discussed further in conjunction with FIG. 1 and other figures and can be integrated with respect to the embodiment discussed herein in conjunction with FIGS. 6-9.

The blockchain configured social federation proxy 606 is configured to retrieve relevant portions of the medical records or social records from the blockchain configured SHRDB 608 in real time. While the blockchain configured SHRDB 608 may be configured to store and manage the social records corresponding to the plurality of entities 102, the blockchain configured social federation proxy 606 may create a virtual view of the storage to the entities 102 through a distributed storage blockchain infrastructure. The blockchain configured social federation proxy 606, upon retrieval of the social records from the blockchain configured SHRDB 608, can display or present them to the entities 102 such that the viewers get a feel as if they are viewing or accessing the blockchain configured SHRDB 608 directly. With this implementation, the blockchain configured social federation proxy 606 may provide a virtual platform for the entities 102 to such as view, access or edit the displayed or presented social records as requested by them through such as displays, presentations, visuals, graphics, and the like. The blockchain configured social federation proxy 606 may pull the social records from the blockchain configured SHRDB 608 for presentation, display, access, view, editing, uploading, sharing, and the like.

In an embodiment, the blockchain configured social federation proxy 606 allows the two-way communication between the entities 102 and the blockchain configured SHRDB 608 by distributing storage and access facility over a wide network at several distributed locations. The blockchain configured SHRDB 608 can collect the health records and healthcare information from several information sources associated with the entities 102. The collected records can be stored in a physical storage of the blockchain configured SHRDB 608. The records stored in the SHRDB 608 can further be accessed at the blockchain configured social federation proxy 606. The entities 102 can enjoy the facility of integration, ingestion, distribution and retrieval of the records all at the same time through the blockchain configured social federation proxy 606 without even knowing that the access is done or the records are routed through two different levels—blockchain configured social federation proxy level and the blockchain configured SHRDB 608. In some embodiments, a virtualization layer may be provided to create a virtual environment that is capable of allowing the entities 102 to share/access/edit or manage records and also view or retrieve the social records from the blockchain configured social federation proxy 606 hiding the difference between the blockchain configured social federation proxy 606 and the blockchain configured SHRDB 608 from the entities 102.

In an embodiment, the policy controller 114 can be operatively and/or communicatively connected with a blockchain validation device 610. The blockchain validation device 610 may use inputs from the policy controller 114 to identify access rules and accordingly execute advanced blockchain validation mechanisms to authorize the entities 102 to access and/or manage health records accessible from the blockchain configured multi-faceted social health care component 604 through the distributed plurality of blockchain configured social federation proxy 606 linked to the blockchain configured SHRDB 608 simultaneously.

The blockchain configured validation device 610 may include a non-volatile computer-readable memory and a processor which may be configured to receive a private key from entity 102. Entity 102 may be authorized to manage the medical records privately using the private key in conjunction with the inputs from and the rules defined by the policy controller 114 for accessing and managing the medical records. One of ordinary skill in the art would recognize there can be a variety of different proof standards that could be used by the blockchain validation device 610. The proof standard may be based on proof of work, such as hash value requirements, proof of stake, such as a key or other indicator of consensus, or any other kind or proof of consensus. The proof standard may be applied as a rule that may require a hash value to be less than the proof standard, more than the proof standard, or have a required bit sequence or a required number of leading or trailing zeroes. Any proof standard may be used without departing from the spirit and scope of the present invention. In an embodiment, the policy controller 114 may be configured within the blockchain validation device 610.

In an embodiment, the medical records or health records or social health records or social records containing contextual health information can be generated from patients, caretakers, care providers, devices, sensors, social networks and the like. The social health records referred herein can be understood as medical records stored in a central storage database such as the SHRDB 608 and the plurality of distributed social federation proxy 606. In an embodiment, the social health records referred herein can be understood as medical records collected from several distinct locations such as several social aware networks or applications or devices and brought at the blockchain configured SHRDB 608 and the associated distributed social federation proxy 606. The social records thus collected and integrated can further be distributed socially among several entities such as users individually or through social networks or applications.

In an embodiment, the blockchain configured SHDRB 608 may contain one or more or all of the components of the SHRDB 106 shown in FIGS. 1 and 4. In an embodiment, the blockchain configured social federation proxy 606 may contain one or more or all of the components of the social federation proxy illustrated in FIG. 4.

The healthcare information sources which generate and/or provide data or social health records or health records to be aggregated and distributed across the blockchain configured SHRDB 608 and the blockchain configured social federation proxy 606 may include a social aware network 118, an environment sensor and/or any other sensor 120, a wearable health monitoring device 122, a GPS-based device 126, and a scanner 124.

In at least some embodiment, the social aware network 118 can be similar to as discussed in conjunction with various figures already. In an embodiment, the social aware network 118 may be defined as a network with an arbitrary large number of networked computers accessing the social network 118 through registered social profiles. The social network 118 facilitates posting and sharing online clinical reviews simultaneously viewable by each of the arbitrary large number of computers including such as a clinical provider computer a patient computer, and the like.

In an embodiment, the social network 118 can function as a source of social records signifying social determinants of health which may become a part of the social records (or health records used interchangeably). In an example, the social records signifying the social determinants of health may be input from any of the entity and get stored in the blockchain configured social federation proxy 606 and the blockchain configured SHRDB 608 which may then be accessed, managed, and edited by any of entity 102 as per access policies maintained by the policy controller 114 and/or the blockchain configured validation device 610. In an embodiment, the social determinants may include details about economic stability such as pertaining to employment, income, expenses, debt, medical bills, and support. In an embodiment, the social determinants may include details about neighborhood and physical environment such as housing, transportation, safety, parks, playgrounds, workability, and the like. In an embodiment, the social determinants may include details about education such as literacy, language, early childhood education, vocational training, higher education, and the like. In an embodiment, the social determinants may include details about food of an entity such as hunger, access to healthy options, and the like. In an embodiment, the social determinants may include details about community and social context such as social integration, support systems, community engagement, discrimination, and the like. In an embodiment, the social determinants may include details about healthcare systems associated with an entity such as health coverage, provider ability, provider linguistic and cultural competency, and quality of care, and the like. In an embodiment, the social determinants may include details about various health outcomes such as mortality, morbidity, life expectancy, healthcare expenditures, health status, functional limitations, and the like.

In various embodiments, various factors may combine together to form the social determinants which may be aggregated from the social networks 118 linked to the blockchain configured social federation proxy 606 and the blockchain configured SHRDB 608. These factors may play an important role in determining health of an individual and may need to be reported to a healthcare provider for facilitating an improved care through the blockchain configured digital ecosystem enabled with the use of the blockchain configured SHRDB 608. Reporting these factors and associated social determinants about an entity such as a patient in the form of social records entering into the blockchain configured SHRDB 608 can allow an enhanced focus on prevention and primary care, support for testing, and spreading of new delivery and payment arrangements, and initiatives to foster sharing among relevant parties based on shared authorized access of the social records at least in part across the blockchain configured distributed digital ecosystem. Social determinants of health may define determinants and conditions in which people are born, grow, live, work and age. They may include factors like socioeconomic status, education, the physical environment, employment, and social support networks, as well as access to health care as discussed above. In an example, by knowing the social determinants about a patient, associated care provider may know in near real time about measures to be taken for ensuring an effective care plan and accordingly can annotate the social records with inputs to be broadcasted by the blockchain configured SHRDB 608 for view and access by the patient in private and the patient can accordingly take an action. For example, children born to parents who have not completed high school are more likely to live in an environment that poses barriers to health. Their neighborhoods are more likely to be unsafe, have exposed garbage or litter, and have poor or dilapidated housing and vandalism which when reported to the healthcare provider through the blockchain configured SHRDB 608 can ensure necessary precautions, advise, and treatment plans be made available. In an embodiment, data about the social determinants may be input by the patient himself. In an embodiment, the data about the social determinants may be extracted from the associated sensors 120 and devices such as weather sensor and the like. In an embodiment, the data about the social determinants may be extracted by cross-referencing associated social networks as discussed elsewhere in the document. In an embodiment, the social determinants may be identified by using geospatial approaches that may allow to predefine social determinants in association with geolocations. As soon as the blockchain configured SHRDB 608 receives the social records from a particular location as identified through associated Global Positioning System (GPS)-based device 126 and geo-tags, the predefined social determinants may be mapped on to the received GPS information and the geo-tags to generate a set of social determinants that may be applicable for the entity who submits the social records or from whom the social records are extracted and monitored. This may allow an automated geospatical-based mapping for determining the social determinants of the entities 102. In an example, the GPS information may be gathered in the form of latitudes and longitudes. In an embodiment, the GPS information may be gathered in the form of ZIP codes of a locality or city or state or district etc. The GPS device and geo-tags are discussed further later in the document in conjunction with certain embodiments.

The health records may be obtained from the environment sensor 120 or any other types of sensors. The environment sensor 120 may extract contextual environment related information about an entity such as $102_1$ and input it into the system through the blockchain configured multi-faceted social healthcare component 604. In an example, the environment sensor 120 may communicatively connect with the multi-faceted social healthcare component 604 and/or the blockchain configured social federation proxy 606 so as to allow integration of the contextual medical or health records into the blockchain configured social federation proxy 606 and the blockchain configured SHRDB 608 automatically. In an embodiment, an entity such as $102_1$ may first extract the contextual medical records from the environment sensor 120 and input them into the blockchain configured social federation proxy 606 and/or blockchain configured SHRDB 608 manually through the blockchain configured multi-faceted social healthcare component 604. In an embodiment, the environment sensor 120 may generate information indicative of environmental conditions associated with entity $102_1$ such as a patient. For, example, a patient may be living in a high polluting environment which may require particular attention from concerned healthcare providers. As soon as the patient inputs this information, the healthcare provider may, in near real-time, get an update and access it through the blockchain configured distributed framework and accordingly make necessary changes in health plans, treatment etc. In an embodiment, the environment sensor 120 may be of various types such as a pollution sensor, moisture sensor, smoke sensor, nitrogen oxide (NOX) sensor, different types of gas sensors, rain sensor, temperature sensor, humidity sensor, pressure sensor, salinity sensor, pH sensor, oxygen sensor, carbon dioxide sensor, fluorescence sensor, light sensor, heat sensor, turbidity sensor, sedimentation sensor, and the like. In various embodiments, the health records may be aggregated from various other types of sensors without limitations.

Another information source for aggregating the health records may be the wearable health monitoring device 122 including such as wearable medical devices, health monitoring devices, internet of things enabled devices (IoT devices) and the like. The wearable health monitoring device 122 may extract individual contextual information from an entity such as a patient during monitoring and analyzing processes and automatically report to the blockchain configured social federation proxy 606.

In an embodiment, the blockchain configured multi-faceted social healthcare component 604 may be may be operatively and communicatively connected with a scanner 124 to allow scanning and ingestion of scanned health records into the system. In particular, off chain medical records that may not be standardized and available in abstract form may require to be scanned by the scanner 124 and then added to the blockchain configured social federation proxy 606. For example, a diagnostic center may scan patient diagnosis reports and ingest them for authorized viewing by the patient and healthcare provider through the blockchain configured multi-faceted social healthcare component 604. In an embodiment, the scanner 124 may be capable of reading barcode information so that the read information may be input into the blockchain configured SHRDB 608.

In an embodiment, the device-driven non-intermediated blockchain configured digital ecosystem 600 (referred to as blockchain configured digital ecosystem 600 interchangeably without limitations) configured to create the social integrity network 602 may power health information exchange facilities and reduce or eliminate the friction and costs of intermediaries. The blockchain configured digital ecosystem 600 provides a secured, disintermediated and distributed framework to amplify and support integration of healthcare information across a range of uses and stakeholders defined by the entity. In accordance with an embodiment, the blockchain configured digital ecosystem 600 may not require human operators and all participants (entity and associated computers and devices) may have access to distributed ledgers to maintain a secure exchange without brokered trust. The blockchain configured digital ecosystem 600 makes the system more efficient and involves lower costs because of disintermediation. The blockchain configured digital ecosystem 600 may facilitate a secured and distributed framework for patient digital identities which may use private and public keys secured through cryptography and thus protecting patient identity by allowing a restricted access to a particular entity in accordance with dynamic rules and policies as discussed earlier herein. The distributed nature of the blockchain configured digital ecosystem 600 enables shared data which may provide near real-time updates across the social integrity network 602 to all the entities 102. A smart contracting consistent with rules-based methods as defined earlier such as in accordance with (a) to (e) without limitations may be executed to accessing patient data that can be permissioned to selected entities.

Figure 7:
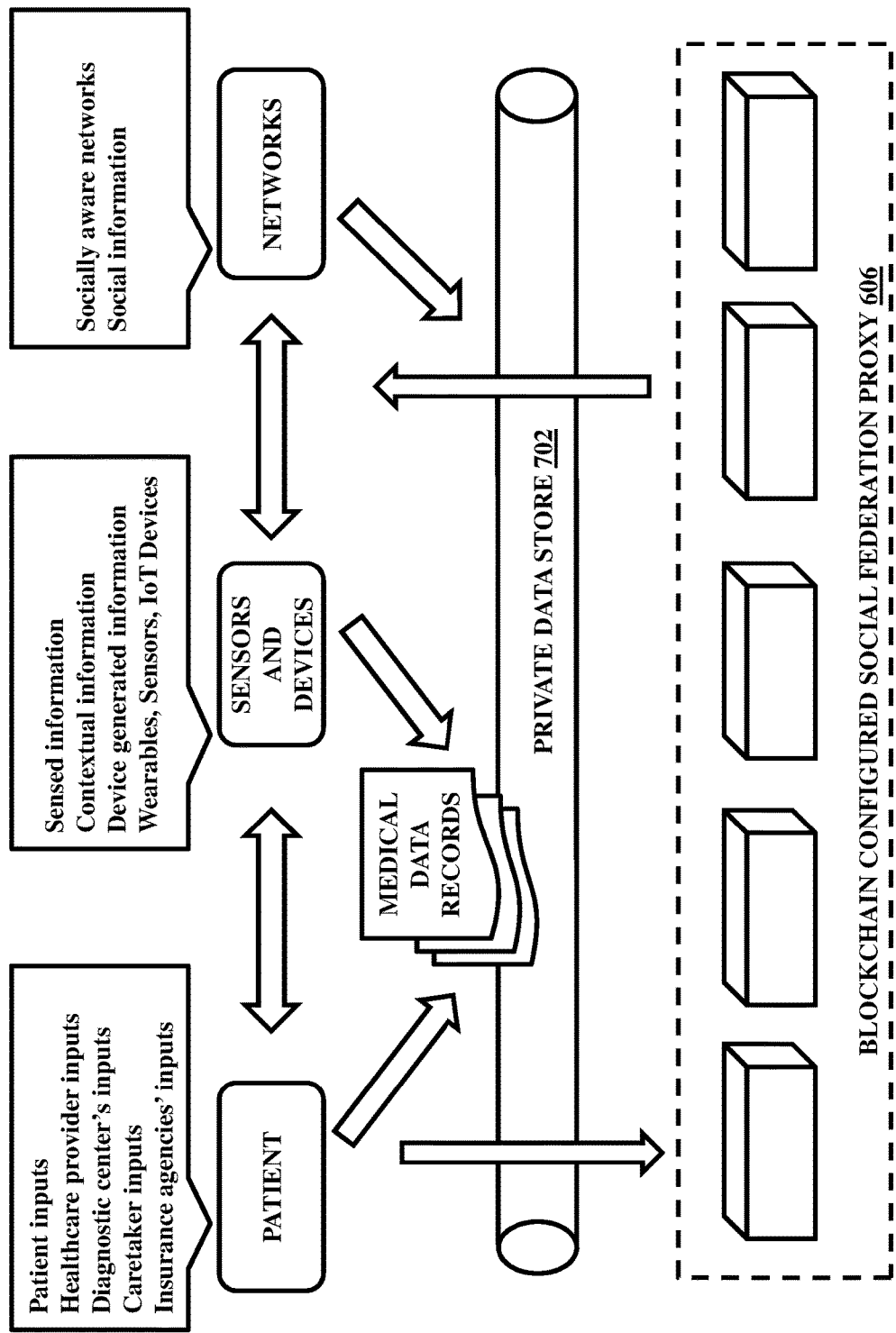
FIG. 7 illustrates an architecture for enabling health care transactions and accessing of social records by the entities in accordance with the blockchain configured digital ecosystem of FIG. 6, in accordance with embodiments herein.

FIG. 7, with reference to FIGS. 1 through 6, illustrates an architecture for enabling health care transactions and accessing of the social records or health records by the entities 102 in accordance with the blockchain capable digital ecosystem 600 as discussed in conjunction with FIG. 6. At least some embodiments for enabling various health care transactions are discussed herein in conjunction with FIGS. 6 and 7.

The blockchain configured social federation proxy 606 may provide a private view referred to as private data store 702 so that each entity 102 can privately access and allow others to access certain medical records as appropriate and authorized based on various policies such as based on (a) to (e) without limitations. Each of the entities 102 may access the medical records through the dedicated private store 702 available through the distributed blockchain configured social federation proxy 606 which may be enabled in the form of distributed blocks as shown in FIG. 7, with each block providing a facility to access the blockchain configured social federation proxy 606 by multiple entities at the same time based on defined and granted access rights through the blockchain configured multi-faceted social health care component 604. The various medical records as accessible by the entities 102 may be aggregated from the entities 102 and respective computing devices and extracted from various devices, sensors, social aware networks, wearables, IoT devices, or provided directly by humans as patient inputs, healthcare provider inputs, diagnostic center's inputs, caretaker inputs, insurance agency's inputs, and the like without limitations such as discussed already in conjunction with FIG. 6.

The private data store 702 may provide a virtual storage to facilitate interaction, information exchange, and presentation of stored health records according to granted access for an entity. For example, while the blockchain configured SHRDB 608 and blockchain configured social federation proxy 606 may store entire health records in a distributed manner, the private data store 702 allows a virtual storage of only limited records out of the entire health records in accordance with permissions granted to entity 102. The virtual view of the health records in the private data store 702 may behave like a distributed relational database referencing to the blockchain configured social federation proxy 606 and the blockchain configured SHRDB 608. The private data store 702 may be configured to auto-hash healthcare interaction at any required interval. This compartmentalization of the health records ensures that the medical records are secured and private as per access rights authorized by owners of the medical records. The data presented on the private data store 702 of the blockchain serves as a secure way to ensure that the private data store 702 is in sync with any permissioned entity's medical records stored in the blockchain configured SHRDB 608 and blockchain configured social federation proxy 606, and as a way for trusted third-parties (entities 102) to discover when there are new medical records that are relevant to the accounts they are entitled and authorized to monitor.

In accordance with an exemplary use case of the current embodiment, a patient may enter his/her health records into the blockchain configured SHRDB 608 by accessing the blockchain configured multi-faceted social health care component 604 or the health records may extracted from associated devices, sensors, scanners, and networks, and moved into the blockchain configured SHRDB 608 and respective blockchain configured social federation proxy 606. The blockchain configured SHRDB 608 may broadcast this update of the health records to relevant and authorized entities with a pointer to the health records. The authorized entities such as a care provider may access the health records and annotate further based on device information extracted from the sensors 120 and devices 122. For example, the care provider may note pollution related information in a patient's area as obtained from a pollution sensor and update treatment plans. These updates from the care provider may be broadcasted by the blockchain configured SHRDB 608 to relevant and authorized entities with a pointer to the updates. The authorized entities such as the patient may access the information and drive his/her treatments accordingly. In an example, any entity may initiate sharing of information through a key exchange to retrieve a shared secret to decrypt the health records and can read authorized health records from the private data store 702.

In an embodiment, the blockchain configured digital ecosystem 600 may provide a federated blockchain consisting of several entities 102 and associated computers and devices and sensors that jointly create the health records or social records and attempts to process transfers of data through a trusted, secured and distributed network of the blockchain configured social federation proxy 606. Such entities 102 can include patients, care takers, care providers, regulators, payers, and the like. Federations can be organized by systems of care such as identified by geography, e.g. community or state. Patients may be assumed to stay within these systems of care that cross organizations. In an example, the federated blockchain may be applied on top of an existing health information exchange community as a way to further reduce costs and help the community reach financial sustainability.

In accordance with an embodiment, the entities 102 can access the health record based on authorization and access rights granted which may dynamically be updated in accordance with embodiments as discussed elsewhere in the document. The blockchain validation device 610 may be configured to validate identity of an entity such as $102_1$ accessing the health records to establish a trusted information exchange and interaction. The blockchain validation device 610 may utilize a variety of identity validation algorithms and schemes such as but not limited to facial expressions, geographical coordinates, geo-tags, gestures, muscle activity, and the like. In accordance with a specific type of validation scheme utilized by the blockchain validation device 610, a validation scheme-based device may be utilized. Two embodiments, in particular, are discussed herein in conjunction with FIG. 6 that provide for the use of geo-tagging and facial expression for validation of the identity of the entities 102.

In an embodiment, the blockchain validation device 610 may obtain geographical coordinates associated with an entity $102_1$ from a global position system (GPS)-based device 126. The blockchain configured SHRDB 608 may tag the medical records associated with entity $102_1$ using geo-tags to establish a geographical identity with the health records and entity $102_1$. The geo-tags may be used to validate identity of entity $102_1$ as well as identity of authorized users to gain access of the health records at least in part. For example, a patient may reside in a particular state of the United States as noted from the patient's demographic information stored in the blockchain configured SHRDB 608. However, if the GPS-based device 126 sends geographical coordinates that indicate another location remote from the United States, the blockchain configured validation device 610 may establish a conflict and may not authorize to ingest the medical records coming from a conflicting geography. The blockchain configured validation device 610 may instruct the blockchain configured SHRDB 608 which may eventually inform the patient for the conflicting information. If the patient is able to satisfy validation and authorization requirements, the medical records may then be accepted or else may remain suspended until the requirements are met. The blockchain configured validation device 610 may include a geo-tagging device 612 which may perform geo-tagging of the medical records and also compare the geo-tags with pre-stored information about the patient for processing validation.

In an embodiment, the blockchain validation device 610 may extract information pertaining to facial expressions of an entity $102_1$ such as a patient from an associated facial expression sensor 614. The facial expression sensor 614 may be of a variety of types to identify and sense a variety of facial expressions as discussed above without limitations. The sensed facial expressions may be communicated to the blockchain configured SHRDB 608 which may be used by a facial expression validation device 616 of the blockchain configured validation device 610 to perform processing of the sensed facial expressions and evaluate genuineness in accordance with predefined facial patterns.

The facial expression sensor 614 (also referred to as face recognition sensor 614 interchangeably) may perform automatic face recognition for surveillance, security, authentication or verification purposes of the entities 102. Information detected by the facial expression sensor 614 may not only expose sensation or passion of a person but can also be used to judge his/her mental views and psychosomatic aspects. The facial expression sensor 614 may employ one or more of different techniques such as motion-based approach, muscle-based approach or any other approach without limitations. These approaches may such as involve analysis of aspects originating from bones, tissues, skin, muscles, deformities, contractions, expansions, and so on. The facial expression sensor 614 may sense the information and transmit the sensed information to the facial expression-based validation device of the blockchain validation device 610 so that the blockchain validation device 610 may identify and verify entity $102_1$ interacting with the blockchain configured social federation proxy 606 based on pre-defined parameters signifying complex facial expressions for genuineness and fraud. These pre-defined parameters and related details may be stored in a memory circuit associated with the blockchain configured SHRDB 608 or the blockchain validation device 610.

Figure 8:
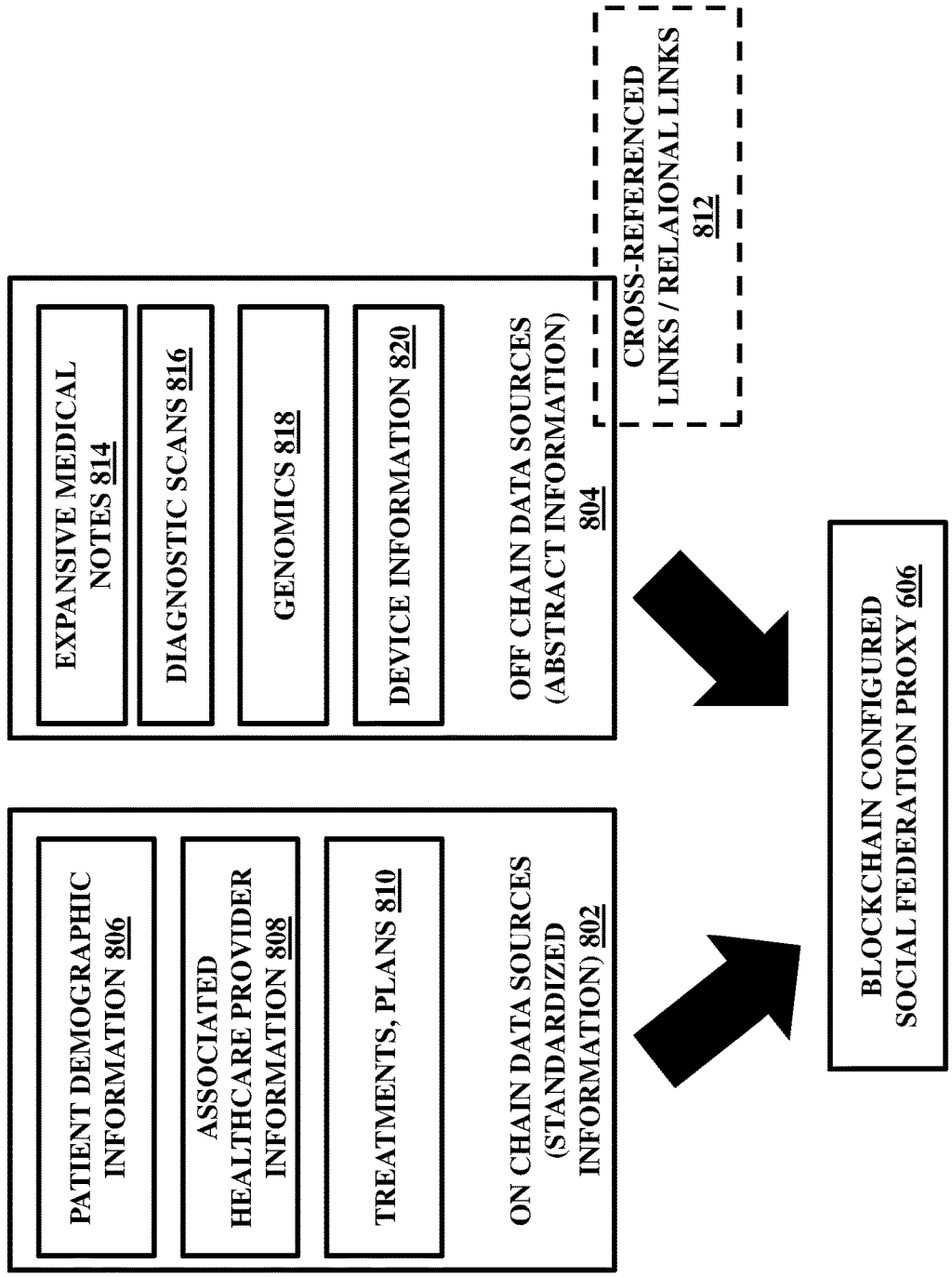
FIG. 8 illustrates exemplary on chain data sources and off chain data sources generating data for storage in and/or accessible through a blockchain configured social health record data bank (SHRDB), in accordance with embodiments herein.

In various embodiments, the information sources (or data sources) accessing and interaction with the blockchain configured multi-faceted social healthcare component 604 may generate information or the social records or the medical records or the health records (used interchangeably) and input the information into the blockchain configured social federation proxy 606 and the blockchain configured SHRDB 608. The information sources can be of two types—on chain data sources 802 and off chain data sources 804 as illustrated in FIG. 8, with reference to FIGS. 1 through 7. The on chain data sources 802 may generate standardized information that may directly be saved on the blockchain configured social federation proxy 606 in the form of standardized and templatized information. Such information may include patient demographic information 806, details or demographic information about healthcare providers 808, standard treatments and health plans 810, and the like. The off chain data sources 804 may generate abstract information that may not be fully or even partially standardized. This type of information may be maintained through relational links 812 so that the information may be stored externally while the relational links 812 may be maintained by the blockchain configured SHRDB 608 and the blockchain configured social federation proxy 606. In this manner, the relational links 812 may facilitate cross-referencing of the health records or stored information and may redirect any access to the external storage. The off chain data sources 804 may generate information such as expansive notes 814 that may not be standardized, for example annotations added by a doctor, diagnostic scans 816 such as generated by the scanner, genomics data 818 involving gene sequencing etc., device information 820 coming from sensors and medical devices or wearables which may not follow a particular format, and the like.

Figure 9:
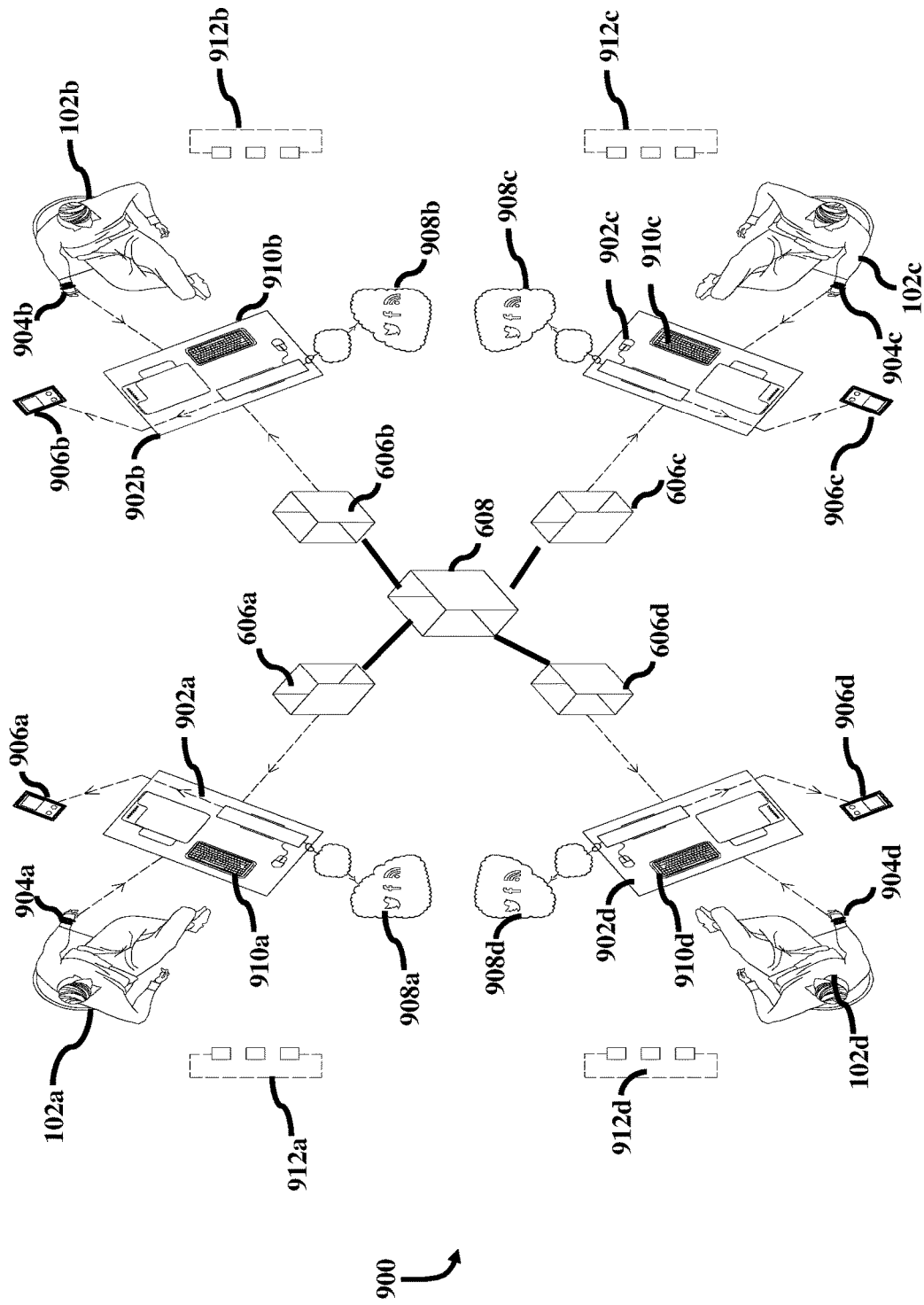
FIG. 9 illustrates another view of a portion of a blockchain configured digital ecosystem illustrating multiple entities and associated networks, devices, and systems, in accordance with embodiments herein.

FIG. 9, with reference to FIGS. 1 through 8, illustrates another view of a portion of the digital ecosystem 600 illustrating multiple entities 102*a*, 102*b*, 102*c*, and 102*d* (together 102); respective associated computing systems 902*a*, 902*b*, 902*c*, and 902*d*; respective associated wearable health monitoring devices 904*a*, 904*b*, 904*c*, and 904*d*; respective associated GPS-based devices 906*a*, 906*b*, 906*c*, and 906*d*; respective associated social networks 908*a*, 908*b*, 908*c*, and 908*d*; respective associated scanners 910*a*, 910*b*, 910*c*, and 910*d*; respective associated sensors 912*a*, 912*b*, 912*c*, and 912*d* communicating with the plurality of blockchain configured social federation proxy 606*a*, 606*b*, 606*c*, and 606*d* and the blockchain configured SHRDB 608 for health information management as discussed in accordance with various embodiment discussed in the document.

The blockchain enabled digital ecosystem 600 may facilitate a slidechain that may allow for multiple valid branches or entities or devices or networks to propagate simultaneously with a customized set of protocol rules embedded in and applied to each such participant in the chain that branch from another chain. The digital ecosystem provides a computer-implemented system for accessing, developing and maintaining a decentralized database through a peer-to-peer network, to preserve the original state of data inputs while adapting to changing circumstances, user preferences, and emerging technological capabilities.

The security of the blockchain-enabled digital ecosystem is increased by implementing it on a distributed integrity network. A large number of participants and entities all have access to the blockchain and all attempts to add blocks to the chain by finding a key that produces a valid hash for a given block of data. Blockchains on a distributed network with sufficiently restrictive rules for creating valid blocks are fairly secure against unauthorized changes to the data stored in them. This makes blockchains particularly useful for recording healthcare transactions.

In an example, the embodiments herein provide a computer program product configured to include a pre-configured set of instructions, which when performed, can result in actions as stated in conjunction with the method(s) described above. In an example, the pre-configured set of instructions can be stored on a tangible non-transitory computer readable medium. In an example, the tangible non-transitory computer readable medium can be configured to include the set of instructions, which when performed by a device, can cause the device to perform acts similar to the ones described here.

The embodiments herein may comprise a computer program product configured to include a pre-configured set of instructions, which when performed, can result in actions as stated in conjunction with the methods described above. In an example, the pre-configured set of instructions can be stored on a tangible non-transitory computer readable medium or a program storage device. In an example, the tangible non-transitory computer readable medium can be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon.

Generally, program modules include routines, programs, components, data structures, objects, and the functions inherent in the design of special-purpose processors, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can include both hardware and software elements. The embodiments that are implemented in software include but are not limited to, firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments herein is depicted in FIG. 10, with reference to FIGS. 1 through 9. This schematic drawing illustrates a hardware configuration of an information handling/computer system 1000 in accordance with an exemplary embodiment herein. The system 1000 comprises at least one processor or central processing unit (CPU) 1010. The CPUs 1010 are interconnected via system bus 1012 to various devices such as a random access memory (RAM) 1014, read-only memory (ROM) 1016, and an input/output (I/O) adapter 1018. The I/O adapter 1018 can connect to peripheral devices, such as disk units 1011 and storage drives 1013, or other program storage devices that are readable by the system. The system 1000 can read the inventive instructions on the program storage devices and follow these instructions to execute the methodology of the embodiments herein. The system 1000 further includes a user interface adapter 1019 that connects a keyboard 1015, mouse 1017, speaker 1024, microphone 1022, and/or other user interface devices such as a touch screen device (not shown) to the bus 1012 to gather user input. Additionally, a communication adapter 1020 connects the bus 1012 to a data processing network 1025, and a display adapter 1021 connects the bus 1012 to a display device 1023, which provides a GUI in accordance with the embodiments herein, or which may be embodied as an output device such as a monitor, printer, or transmitter, for example. Further, a transceiver 1026, a signal comparator 1027, and a signal converter 1028 may be connected with the bus 1012 for processing, transmission, receipt, comparison, and conversion of electric or electronic signals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A blockchain validation system comprising:
   a plurality of computing systems connected with a social integrity network;
   a plurality of sub-systems of data records, said plurality of sub-systems comprising:
      a plurality of social aware networks;
      a plurality of sensors;
      a plurality of wearable devices,
      a plurality of scanners,
      wherein each of said plurality of social aware networks, plurality of sensors, plurality of wearable devices, and plurality of scanners serve as a provider of said data records;
   a blockchain configured data bank (BCDB) hosted on a server accessible by each of said plurality of computing systems based on rules and preferences of a plurality of entities upon authorization by said BCDB, wherein said plurality of entities subscribe with said BCDB to create, store, edit, manage or control said data records, said BCDB comprising:
      a computer processing component executing stored computer-implemented instructions to process said data records of said plurality of entities over said social integrity network, said data records obtained from said plurality of social aware networks, said plurality of sensors, said plurality of wearable devices, and said plurality of scanners associated with said entities; and
      a hardware repository coupled to said BCDB to store said data records of said plurality of entities collected from said plurality of social aware networks, said plurality of sensors, said plurality of wearable devices, and said plurality of scanners;
   a blockchain configured component communicatively coupled to said BCDB and adapted to be accessible by each of said plurality of computing systems such that said blockchain configured component enables social interaction among said entities by bypassing said BCDB, and communication with said BCDB over said social integrity network for data records transfer; and
   a plurality of blockchain configured social federation proxies communicatively coupled to said BCDB and said social integrity network and configured to retrieve said data records from said BCDB collected from said plurality of social aware networks, said plurality of sensors, said plurality of wearable devices, and said plurality of scanners, and distribute them to said plurality of social aware networks and said plurality of computing systems for display to said respective plurality of entities upon request and validation, wherein said plurality of blockchain configured social federation proxies comprise a virtualization layer to provide a distributed virtual access of storage of said data records retrieved from said BCDB and allow an indirect access of said plurality of entities to said BCDB, and wherein said plurality of blockchain configured social federation proxies comprise a processing device configured to manage and communicate said data records in a blockchain configured distributed framework;
   a blockchain validation device configured to receive digital inputs from said BCDB to identify access rules and execute blockchain validation mechanisms to authorize said plurality of entities to access said data records accessible from said blockchain configured component through said distributed plurality of blockchain configured social federation proxies linked to said BCDB simultaneously, wherein said blockchain validation device comprises:
      a face recognition device to process information received from respective facial expression sensors associated with said plurality of entities to verify identity of said plurality of entities based on respective facial expressions; and
      a geo-tagging device to obtain geographical coordinates from respective global position system (GPS)-based devices associated with said plurality of entities, tag said data records using geo-tags to establish a geographical identity with said data records, and validate identity of said plurality of entities and said respective data records based on geographical patterns;

wherein said BCDB and said plurality of blockchain configured social federation proxies are further configured to:
  identify a source and a target, wherein said source identifies data records for sharing and said target identifies a computing system out of said plurality of computing systems as a recipient of said data records defined by said source, wherein said identification of at least one of said source and said target is dependent on:
    (a) a permission from an owner of said source;
    (b) an indication of an extent of sharing;
    (c) a nature and characteristic of said target;
    (d) a purpose of said sharing of said data records to said target; and
    (e) a timeframe for allowance of sharing of said data records,
    wherein said source and said target are determined based on (a) to (e) upon receipt of a request from said owner entity, and wherein said sharing of said data records with said target is limited to said timeframe;
  allow partial viewing of said data records corresponding to said source by said target based on (a) to (e);
  stop any viewing based on (a) to (e);
  select which parts to view based on (a) to (e); and
  determine or facilitate said owner entity of said data records to determine who has viewed said data records and accordingly redefine said (a) to (e) and also accordingly make a decision about said partial viewing of said data records corresponding to said source by said target based on (a) to (e) and stopping of any viewing or selecting which parts to view based on said redefined (a) to (e);
  wherein said blockchain configured component is configured to identify who has viewed said data records in real time and share information about who has viewed said data records with said owner in real time, such that said owner allows fully or partially or stops viewing of said data records by said target in real time.

2. The blockchain validation system of claim 1, further comprising a digitized policy controller that is configured to generate an output based on said rules and preferences of said plurality of entities, upon receipt of a request to access said BCDB, said output used by said blockchain configured component to authorize and control access of said plurality of entities.

3. The blockchain validation system of claim 2, further comprising a computerized report generator to generate said data records and computerized reports based on said generated data records from said hardware repository based on said request from said plurality of entities, wherein said computerized reports are approved by said digitized policy controller before sharing with said plurality of entities.

4. The blockchain validation system of claim 1, wherein said blockchain configured component is configured to provide an interactive social user interface comprising a communication module to facilitate said plurality of entities to socially communicate with each other and with said BCDB through an active social communication network such that any of a social cloud and network platform is configured to communicate among said different entities and said BCDB and said plurality of blockchain configured social federation proxies.

5. The blockchain validation system of claim 1, wherein said blockchain configured component further comprises a natural language and speech recognition module to facilitate said plurality of entities to actively interact with each other and with said BCDB through said plurality of blockchain configured social federation proxies using any of natural language and speech recognition.

6. The blockchain validation system of claim 1, wherein said multi-faceted blockchain configured component further comprises a single computerized sign on module for a plurality of social network electronic applications, wherein said blockchain configured component is configured to integrate said plurality of entities with a plurality of social network electronic applications through said single computerized sign on module, and wherein said single computerized sign in module allows any of said plurality of entities to access said data records by signing in any of said plurality of social network electronic applications.

7. The blockchain validation system of claim 1, wherein said target is allowed to view a 'no objection' segment of said data records without restriction within a defined time after initiation of viewing, and wherein said data records corresponding to said 'no objection' segment is further defined by said owner based on (a) to (e).

8. The blockchain validation system of claim 1, wherein said GPS-based devices are associated with said plurality of entities such that said GPS-based devices send signals to said blockchain configured validation device, and wherein said signals are indicative of geographical coordinates of a location where said data records originate.

9. The blockchain validation system of claim 1, wherein said plurality of facial expression sensors are associated with said plurality of entities such that said plurality of facial expression sensors identify and sense a variety of facial expressions to generate electronic signals indicative of sensed facial expressions, and wherein said sensed facial expressions are communicated to said BCDB to be used by said face recognition device of said blockchain configured validation device to perform digital processing of said sensed facial expressions and verify an identity of said plurality of entities in accordance with predefined facial patterns.

10. The blockchain validation system of claim 1, wherein said plurality of sensors comprise any of an environment sensor, a weather sensor, and a pollution sensor, and wherein said plurality of sensors extract contextual information indicative of a plurality of social determinants associated with said plurality of entities.

11. The blockchain validation system of claim 10, wherein said plurality of scanners are communicatively and operatively connected with said plurality of computing systems to scan at least a portion of said data records and transfer said scanned data records into said plurality of blockchain configured social federation proxies and said BCDB.

12. The blockchain validation system of claim 1, wherein said data records comprise a first portion that is standardized and defined in accordance with a template by said BCDB such that said first portion of said data records is on said plurality of said blockchain configured social federation proxies and said BCDB.

13. The blockchain validation system of claim 12, wherein said data records comprise a second portion that is non-standardized and input in said BCDB in a non-standardized format such that said second portion of said data records are stored at an external storage location.

14. The blockchain validation system of claim 13, wherein respective cross-references are maintained by said plurality of blockchain configured social federation proxies and said BCDB so that an access to said cross-references by said plurality of entities is redirected to said external storage location for viewing, accessing, and managing of said second portion of said data records.

\* \* \* \* \*